US006872559B2

(12) United States Patent
Welch et al.

(10) Patent No.: US 6,872,559 B2
(45) Date of Patent: Mar. 29, 2005

(54) E. COLI O157:H7 C1 ESTERASE INHIBITOR-BINDING PROTEIN AND METHODS OF USE

(75) Inventors: Rodney A. Welch, Madison, WI (US); Wyndham W. Lathem, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 112 days.

(21) Appl. No.: 10/002,309

(22) Filed: Oct. 26, 2001

(65) Prior Publication Data

US 2002/0160433 A1 Oct. 31, 2002

Related U.S. Application Data
(60) Provisional application No. 60/243,675, filed on Oct. 26, 2000.

(51) Int. Cl.[7] .......................... C12N 9/48; C12N 15/09; C12P 21/06; C07H 21/04; A61K 38/00
(52) U.S. Cl. ..................... 435/212; 435/69.1; 435/69.2; 435/7.37; 536/23.1; 536/23.2; 530/300; 530/350
(58) Field of Search ............................... 435/212, 69.1, 435/69.2, 7.37; 536/23.1, 23.2; 500/300, 350

(56) References Cited

PUBLICATIONS

Makino et al. [DNA Research 5 : 1–9, (1998)] {including sequence search alignment between T43121 and SEQ ID NO : 2).*
Sequence search alignment between Q9ZAL1 (5.1.1999) and SEQ ID NO : 2 (residue 24–886).*
Burland V, et al., "*Escherichia coli* 0157:H7 plasmid p0157, complete sequence" Database EMBL Online Database Entry AF074613, Nov. 4, 1998.
Brunder, W., "*E. coli* 3.3 kb DNA fragment from plasmid p0157", Database Accession No. Y11831, Database EMBL Online Database Entry EC33P0157, Jun. 30, 1999.
Brunder W., "Hypothetical 34.0 kDa protein (Fragment)" Database Accession No. Q9ZAL1, May 1, 1999.
Lathem W.W., et al., "A novel metalloprotease secreted by *Escherichia coli* 0157:H7 cleaves C1 esterase inhibits regulator of multiple proteolytic cascades", Abstracts of the General Meeting of the American Society for Microbiolo vol. 101, p. 113, May 20–24, 2001.
Witowski, S.E., et al., "StcE, a novel metalloprotease from enterohemorrhagic *Escherichia coli*, is specific for p containing strains of diarrheagenic *E. coli*", Abstracts of the General Meeting of the American Society for Microbiology vol. 101, p. 113, May 20–24, 2001.

Perna, N. T., Plunkett III, G., Burland, V., Mau, B., Glasner, J. D., Rose, D. J., Kirkpatrick, H. A., Postal, G., Hackett, J., Klink, S., Boutin, A., Shao, Y., Miller, L., Grotbeck, E. J., Davis, N. W., Lim, A., Dimalanta, E. T., Potamousis, K. D., Apodaca, J., Anantharaman, T. S., Lin, J., Yen, G., Schwartz, D. C., Welch, R. A. & Blattner, F. R. (2001) *Nature* 409, 529–533.
Waytes, A. T., Rosen, F. S. & Frank, M. M. (1996) *N. Engl. J. Med.* 334, 1630–1634.
Caliezi, C., Wuillemin, W. A., Zeerleder, S., Redondo, M., Eisele, B. & Hack, C. E. (2000) *Pharmacol. Rev.* 52, 91–112.
Poulle, M., Burnouf–Radosevich, M. & Burnouf, T. (1994) *Blood Coagulation & Fibrinolysis* 5, 543–9.
Kuno, K., Terashima, Y. & Matsushima, K. (1999) *Journal of Biological Chemistry* 274, 18821–6.
Gadek, J. E., Hosea, S. W., Gelfand, J. A., Santaella, M., Wickerhauser, M., Triantaphyllopoulos, D. C. & Frank, M. M. (1980) *N. Engl. J. Med.* 302, 542–546.
De Lorenzo, V. D. & Timmis, K. N. (1994) in *Bacterial Pathogenesis*, eds. Clark, V. L. & Bavoil, P. M. (Academic Press, San Diego), vol. 235. pp. 386–405.
O'Farrell, P. H. (1975) *J Biol Chem* 250, 4007–21.
Bauer, M. E. & Welch, R. A. (1996) *Infect. Immun.* 64, 167–175.
Burland, V., Shao, Y., Perna, N. T., Plunkett, G., Sofia, H. J. & Blattner, F. R. (1998) *Nucleic Acids Research* 26, 4196–4204.
Roesch, P. L. & Blomfield, I. C. (1998) *Molecular Microbiology* 27, 751–61.
Catanese, J. & Kress, L. F. (1984) *Biochim. Biophys. Acta* 789, 37–43.
Karmali, M. A., Petric, M., Steele, B. T. & Lim, C. (1983) *Lancet* 1, 619–620.
Caprioli, A., Luzzi, I., Gianviti, A., Russmann, H. & Karch, H. (1995) *J. Med. Microbiol.* 43, 348–353.
Jiang, W. & Bond, J. S. (1992) *FEBS Lett* 312, 110–114.
Jung, C.–M., Matsushita, O., Katayama, S., Minami, J., Sakurai, J. & Okabe, A. (1999) *J. Bact.* 181, 2816–2822.

* cited by examiner

*Primary Examiner*—Tekchand Saidha
(74) *Attorney, Agent, or Firm*—Michael Best & Friedrich LLP; Teresa J. Welch; Jill A. Fahrlander

(57) ABSTRACT

Disclosed is a pO157 plasmid-specified polypeptide found in *E. coli* EDL933and other enterohemorrhagic *E. coli* that binds to and cleaves C1-esterase inhibitor. Also disclosed are methods employing the polypeptide for diagnosing and treating colitis or hemolytic uremic syndrome, and methods of detecting potential therapeutics.

11 Claims, 11 Drawing Sheets

Lysates of *E. coli* strains containing pO157 induce the aggregation of Jurkat cells, while non-pO157-containing *E. coli* lysates do not aggregate the same cells.

Purification of StcE-His from WAM2572

StcE is produced by strains of *E. coli* that carry pO157 but not in strains that lack pO157 or have a transposon insertion in *stcE*.

StcE – His interacts with a human serum protein(s) of approximately 105 kDa.

Figure 5. StcE-His cleaves C1 inhibitor in human serum.

Differential digestion patterns of C1-INH by StcE-His and *P. aeruginosa* elastase.

FIG. 6

Detection of StcE in fecal filtrates from children with diarrhea.

StcE E435D-His lacks proteolytic activity against and the ability to bind to C1-INH.

Figure 9. PCR analysis of *stcE* in the DEC collection.

Detection of StcE in bacterial-conditioned culture supernatants.

Detection of C1-INH proteolytic activity in bacterial-conditioned culture supernatants.

SEQUENCE LISTING

<160> NUMBER OF SEQ ID NOS: 17

<210> SEQ ID NO 1
<211> LENGTH: 2798
<212> TYPE: DNA
<213> ORGANISM: Unknown
<220> FEATURE:
<223> OTHER INFORMATION: Description of Unknown Organism: E. coli O157:H7 plasmid pO157
<220> FEATURE:
<221> NAME/KEY: CDS
<222> LOCATION: (138)..(2798)
<223> OTHER INFORMATION:

<400> SEQUENCE: 1

```
tttacgaaac aggtgtaaat atgttataaa aataaccaac gactagtgaa taagtcgctc      60
ctgaaaaaat aaaatataga aatactgtta tatccggctg catgaacact aaaatgaatg     120
agagatggag aacaccg atg aaa tta aag tat ctg tca tgt acg atc ctt        170
                   Met Lys Leu Lys Tyr Leu Ser Cys Thr Ile Leu
                    1               5                  10 gcc cct ctg gcg att ggg gta ttt tct gca aca gct gct gat aat aat       218
Ala Pro Leu Ala Ile Gly Val Phe Ser Ala Thr Ala Ala Asp Asn Asn
              15                  20                  25 tca gcc att tat ttc aat acc tcc cag cct ata aat gat ctg cag ggt       266
Ser Ala Ile Tyr Phe Asn Thr Ser Gln Pro Ile Asn Asp Leu Gln Gly
         30                  35                  40 tcg ttg gcc gca gag gtg aaa ttt gca caa agc cag att tta ccc gcc       314
Ser Leu Ala Ala Glu Val Lys Phe Ala Gln Ser Gln Ile Leu Pro Ala
     45                  50                  55 cat cct aaa gaa ggg gat agt caa cca cat ctg acc agc ctg cgg aaa       362
His Pro Lys Glu Gly Asp Ser Gln Pro His Leu Thr Ser Leu Arg Lys
 60                  65                  70                  75 agt ctg ctg ctt gtc cgt ccg gtg aaa gct gat gat aaa aca cct gtt       410
Ser Leu Leu Leu Val Arg Pro Val Lys Ala Asp Asp Lys Thr Pro Val
                 80                  85                  90 cag gtg gaa gcc cgc gat gat aat aat aaa att ctc ggt acg tta acc       458
```

```
                    Gln Val Glu Ala Arg Asp Asp Asn Asn Lys Ile Leu Gly Thr Leu Thr
                                 95                 100                 105 ctt tat cct cct tca tca cta ccg gat aca atc tac cat ctg gat ggt           506
Leu Tyr Pro Pro Ser Ser Leu Pro Asp Thr Ile Tyr His Leu Asp Gly
            110                 115                 120 gtt ccg gaa ggt ggt atc gat ttc aca cct cat aat gga acg aaa aag           554
Val Pro Glu Gly Gly Ile Asp Phe Thr Pro His Asn Gly Thr Lys Lys
        125                 130                 135 atc att aat acg gtg gct gaa gta aac aaa ctc agt gat gcc agc ggg           602
Ile Ile Asn Thr Val Ala Glu Val Asn Lys Leu Ser Asp Ala Ser Gly
140                 145                 150                 155 agt tct att cat agc cat cta aca aat aat gca ctg gtg gag atc cat           650
Ser Ser Ile His Ser His Leu Thr Asn Asn Ala Leu Val Glu Ile His
                    160                 165                 170 act gca aat ggt cgt tgg gta aga gac att tat ctg ccg cag gga ccc           698
Thr Ala Asn Gly Arg Trp Val Arg Asp Ile Tyr Leu Pro Gln Gly Pro
                175                 180                 185 gac ctt gaa ggt aag atg gtt cgc ttt gtt tcg tct gca ggc tat agt           746
Asp Leu Glu Gly Lys Met Val Arg Phe Val Ser Ser Ala Gly Tyr Ser
            190                 195                 200 tca acg gtt ttt tat ggt gat cga aaa gtc aca ctc tcg gtg ggt aac           794
Ser Thr Val Phe Tyr Gly Asp Arg Lys Val Thr Leu Ser Val Gly Asn
        205                 210                 215 act ctt ctg ttc aaa tat gta aat ggt cag tgg ttc cgc tcc ggt gaa           842
Thr Leu Leu Phe Lys Tyr Val Asn Gly Gln Trp Phe Arg Ser Gly Glu
220                 225                 230                 235 ctg gag aat aat cga atc act tat gct cag cat att tgg agt gct gaa           890
Leu Glu Asn Asn Arg Ile Thr Tyr Ala Gln His Ile Trp Ser Ala Glu
                    240                 245                 250 ctg cct gcg cac tgg atc gtg cct ggt tta aac ttg gtg att aaa cag           938
Leu Pro Ala His Trp Ile Val Pro Gly Leu Asn Leu Val Ile Lys Gln
                255                 260                 265 ggc aat ctg agc ggt cgc cta aat gat atc aag att gga gca ccg ggt           986
Gly Asn Leu Ser Gly Arg Leu Asn Asp Ile Lys Ile Gly Ala Pro Gly
            270                 275                 280 gag ctg ttg ttg cat aca att gat atc ggg atg ttg acc act ccc cgg          1034
Glu Leu Leu Leu His Thr Ile Asp Ile Gly Met Leu Thr Thr Pro Arg
        285                 290                 295 gat cgc ttt gat ttt gcc aaa gac aaa gaa gca cat agg gaa tat ttc          1082
Asp Arg Phe Asp Phe Ala Lys Asp Lys Glu Ala His Arg Glu Tyr Phe
300                 305                 310                 315 cag acc att cct gta agt cgt atg att gtt aat aat tat gcg cct cta          1130
Gln Thr Ile Pro Val Ser Arg Met Ile Val Asn Asn Tyr Ala Pro Leu
                    320                 325                 330 cac cta aag gaa gtt atg tta cca acc gga gag tta ttg aca gat atg          1178
His Leu Lys Glu Val Met Leu Pro Thr Gly Glu Leu Leu Thr Asp Met
                335                 340                 345 gat cca gga aat ggt ggg tgg cat agt ggt aca atg cgt caa aga ata          1226
Asp Pro Gly Asn Gly Gly Trp His Ser Gly Thr Met Arg Gln Arg Ile
            350                 355                 360 ggt aaa gaa ttg gtt tcg cat ggc att gat aat gct aac tat ggt tta          1274
Gly Lys Glu Leu Val Ser His Gly Ile Asp Asn Ala Asn Tyr Gly Leu
        365                 370                 375 aat agt acc gca ggc tta ggg gag aat agt cat cca tat gta gtt gcg          1322
Asn Ser Thr Ala Gly Leu Gly Glu Asn Ser His Pro Tyr Val Val Ala
380                 385                 390                 395 caa tta gcg gca cat aat agc cgc ggt aat tat gct aat ggc atc cag          1370
Gln Leu Ala Ala His Asn Ser Arg Gly Asn Tyr Ala Asn Gly Ile Gln
                    400                 405                 410
```

```
                                                        -continued
gtt cat ggt ggc tcc gga ggt ggg gga att gtt act tta gat tcc aca     1418
Val His Gly Gly Ser Gly Gly Gly Gly Ile Val Thr Leu Asp Ser Thr
        415                 420                 425 ttg ggg aat gag ttc agt cat gaa gtt ggt cat aat tat ggt ctt ggt     1466
Leu Gly Asn Glu Phe Ser His Glu Val Gly His Asn Tyr Gly Leu Gly
        430                 435                 440 cat tat gta gat ggt ttc aag ggt tct gta cat cgt agt gca gaa aat     1514
His Tyr Val Asp Gly Phe Lys Gly Ser Val His Arg Ser Ala Glu Asn
        445                 450                 455 aac aac tca act tgg gga tgg gat ggt gat aaa aaa cgg ttt att cct     1562
Asn Asn Ser Thr Trp Gly Trp Asp Gly Asp Lys Lys Arg Phe Ile Pro
460                 465                 470                 475 aac ttt tat ccg tct caa aca aat gaa aag agt tgt ctg aat aat cag     1610
Asn Phe Tyr Pro Ser Gln Thr Asn Glu Lys Ser Cys Leu Asn Asn Gln
                480                 485                 490 tgt caa gaa ccg ttt gat gga cac aaa ttt ggt ttt gac gcc atg gcg     1658
Cys Gln Glu Pro Phe Asp Gly His Lys Phe Gly Phe Asp Ala Met Ala
            495                 500                 505 gga ggc agc cct ttc tct gct gca aac cgt ttc aca atg tat act ccg     1706
Gly Gly Ser Pro Phe Ser Ala Ala Asn Arg Phe Thr Met Tyr Thr Pro
        510                 515                 520 aat tca tcg gct atc atc cag cgt ttt ttt gaa aat aaa gct gtg ttc     1754
Asn Ser Ser Ala Ile Ile Gln Arg Phe Phe Glu Asn Lys Ala Val Phe
        525                 530                 535 gat agc cgt tcc tcc acc ggc ttc agc aag tgg aat gca gat acg cag     1802
Asp Ser Arg Ser Ser Thr Gly Phe Ser Lys Trp Asn Ala Asp Thr Gln
540                 545                 550                 555 gaa atg gaa ccg tat gaa cac acc att gac cgt gcg gag cag att acg     1850
Glu Met Glu Pro Tyr Glu His Thr Ile Asp Arg Ala Glu Gln Ile Thr
                560                 565                 570 gct tca gtc aat gag cta agt gaa agc aaa atg gct gag ctg atg gca     1898
Ala Ser Val Asn Glu Leu Ser Glu Ser Lys Met Ala Glu Leu Met Ala
            575                 580                 585 gag tac gct gtc gtc aaa gtg cat atg tgg aac ggt aac tgg aca aga     1946
Glu Tyr Ala Val Val Lys Val His Met Trp Asn Gly Asn Trp Thr Arg
        590                 595                 600 aac atc tat atc cct aca gcc tcc gca gat aat aga ggc agt atc ctg     1994
Asn Ile Tyr Ile Pro Thr Ala Ser Ala Asp Asn Arg Gly Ser Ile Leu
        605                 610                 615 acc atc aac cat gag gcc ggt tat aat agt tat ctg ttt ata aat ggt     2042
Thr Ile Asn His Glu Ala Gly Tyr Asn Ser Tyr Leu Phe Ile Asn Gly
620                 625                 630                 635 gac gaa aag gtc gtt tcc cag ggg tat aaa aag agc ttt gtt tcc gat     2090
Asp Glu Lys Val Val Ser Gln Gly Tyr Lys Lys Ser Phe Val Ser Asp
                640                 645                 650 ggt cag ttc tgg aaa gaa cgt gat gtg gtt gat act cgt gaa gcg cgt     2138
Gly Gln Phe Trp Lys Glu Arg Asp Val Val Asp Thr Arg Glu Ala Arg
            655                 660                 665 aag cca gag cag ttt ggt gtt cct gtg acg acc ctg gtg ggg tat tac     2186
Lys Pro Glu Gln Phe Gly Val Pro Val Thr Thr Leu Val Gly Tyr Tyr
        670                 675                 680 gat ccg gaa ggc acg ctg tca agc tac atc tat cct gcg atg tat ggt     2234
Asp Pro Glu Gly Thr Leu Ser Ser Tyr Ile Tyr Pro Ala Met Tyr Gly
        685                 690                 695 gcc tat ggc ttc act tat tcc gat gat agt cag aat cta tcc gat aac     2282
Ala Tyr Gly Phe Thr Tyr Ser Asp Asp Ser Gln Asn Leu Ser Asp Asn
700                 705                 710                 715 gac tgc cag ctg cag gtg gat acg aaa gaa ggg cag ttg cga ttc aga     2330
Asp Cys Gln Leu Gln Val Asp Thr Lys Glu Gly Gln Leu Arg Phe Arg
                720                 725                 730
```

```
ctg gct aat cac cgg gct aac aac act gta atg aat aag ttc cat att      2378
Leu Ala Asn His Arg Ala Asn Asn Thr Val Met Asn Lys Phe His Ile
            735                 740                 745 aac gtg cca aca gaa agt cag ccc aca cag gcc aca ttg gtt tgc aat      2426
Asn Val Pro Thr Glu Ser Gln Pro Thr Gln Ala Thr Leu Val Cys Asn
                750                 755                 760 aac aag ata ctg gat acc aaa tcg ctc aca cct gcg cca gaa gga ctt      2474
Asn Lys Ile Leu Asp Thr Lys Ser Leu Thr Pro Ala Pro Glu Gly Leu
        765                 770                 775 acc tat act gta aat ggg cag gca ctt cca gca aaa gaa aac gag gga      2522
Thr Tyr Thr Val Asn Gly Gln Ala Leu Pro Ala Lys Glu Asn Glu Gly
780                 785                 790                 795 tgc atc gtg tcc gtg aat tca ggt aaa cgt tac tgt ttg ccg gtt ggt      2570
Cys Ile Val Ser Val Asn Ser Gly Lys Arg Tyr Cys Leu Pro Val Gly
                800                 805                 810 caa cgg tca gga tat agc ctt cct gac tgg att gtt ggg cag gaa gtc      2618
Gln Arg Ser Gly Tyr Ser Leu Pro Asp Trp Ile Val Gly Gln Glu Val
            815                 820                 825 tat gtc gac agc ggg gct aaa gcg aaa gtg ctg ctt tct gac tgg gat      2666
Tyr Val Asp Ser Gly Ala Lys Ala Lys Val Leu Leu Ser Asp Trp Asp
830                 835                 840 aac ctg tcc tat aac agg att ggt gag ttt gta ggt aat gtg aac cca      2714
Asn Leu Ser Tyr Asn Arg Ile Gly Glu Phe Val Gly Asn Val Asn Pro
        845                 850                 855 gct gat atg aaa aaa gtt aaa gcc tgg aac gga cag tat ttg gac ttc      2762
Ala Asp Met Lys Lys Val Lys Ala Trp Asn Gly Gln Tyr Leu Asp Phe
860                 865                 870                 875 agt aaa cct agg tca atg agg gtt gta tat aaa taa                      2798
Ser Lys Pro Arg Ser Met Arg Val Val Tyr Lys
                880                 885
```

<210> SEQ ID NO 2
<211> LENGTH: 886
<212> TYPE: PRT
<213> ORGANISM: Unknown
<220> FEATURE:
<223> OTHER INFORMATION: Description of Unknown Organism: E. coli O157:H7
      plasmid pO157

<400> SEQUENCE: 2

```
Met Lys Leu Lys Tyr Leu Ser Cys Thr Ile Leu Ala Pro Leu Ala Ile
1               5                   10                  15

Gly Val Phe Ser Ala Thr Ala Ala Asp Asn Asn Ser Ala Ile Tyr Phe
            20                  25                  30

Asn Thr Ser Gln Pro Ile Asn Asp Leu Gln Gly Ser Leu Ala Ala Glu
        35                  40                  45

Val Lys Phe Ala Gln Ser Gln Ile Leu Pro Ala His Pro Lys Glu Gly
    50                  55                  60

Asp Ser Gln Pro His Leu Thr Ser Leu Arg Lys Ser Leu Leu Leu Val
65                  70                  75                  80

Arg Pro Val Lys Ala Asp Asp Lys Thr Pro Val Gln Val Glu Ala Arg
                85                  90                  95

Asp Asp Asn Asn Lys Ile Leu Gly Thr Leu Thr Leu Tyr Pro Pro Ser
            100                 105                 110

Ser Leu Pro Asp Thr Ile Tyr His Leu Asp Gly Val Pro Glu Gly Gly
        115                 120                 125

Ile Asp Phe Thr Pro His Asn Gly Thr Lys Lys Ile Ile Asn Thr Val
130                 135                 140
```

-continued

```
Ala Glu Val Asn Lys Leu Ser Asp Ala Ser Gly Ser Ser Ile His Ser
145                 150                 155                 160

His Leu Thr Asn Asn Ala Leu Val Glu Ile His Thr Ala Asn Gly Arg
                165                 170                 175

Trp Val Arg Asp Ile Tyr Leu Pro Gln Gly Pro Asp Leu Glu Gly Lys
            180                 185                 190

Met Val Arg Phe Val Ser Ser Ala Gly Tyr Ser Ser Thr Val Phe Tyr
        195                 200                 205

Gly Asp Arg Lys Val Thr Leu Ser Val Gly Asn Thr Leu Leu Phe Lys
    210                 215                 220

Tyr Val Asn Gly Gln Trp Phe Arg Ser Gly Glu Leu Glu Asn Asn Arg
225                 230                 235                 240

Ile Thr Tyr Ala Gln His Ile Trp Ser Ala Glu Leu Pro Ala His Trp
                245                 250                 255

Ile Val Pro Gly Leu Asn Leu Val Ile Lys Gln Gly Asn Leu Ser Gly
            260                 265                 270

Arg Leu Asn Asp Ile Lys Ile Gly Ala Pro Gly Glu Leu Leu Leu His
        275                 280                 285

Thr Ile Asp Ile Gly Met Leu Thr Thr Pro Arg Asp Arg Phe Asp Phe
290                 295                 300

Ala Lys Asp Lys Glu Ala His Arg Glu Tyr Phe Gln Thr Ile Pro Val
305                 310                 315                 320

Ser Arg Met Ile Val Asn Asn Tyr Ala Pro Leu His Leu Lys Glu Val
                325                 330                 335

Met Leu Pro Thr Gly Glu Leu Leu Thr Asp Met Asp Pro Gly Asn Gly
            340                 345                 350

Gly Trp His Ser Gly Thr Met Arg Gln Arg Ile Gly Lys Glu Leu Val
        355                 360                 365

Ser His Gly Ile Asp Asn Ala Asn Tyr Gly Leu Asn Ser Thr Ala Gly
    370                 375                 380

Leu Gly Glu Asn Ser His Pro Tyr Val Val Ala Gln Leu Ala Ala His
385                 390                 395                 400

Asn Ser Arg Gly Asn Tyr Ala Asn Gly Ile Gln Val His Gly Gly Ser
                405                 410                 415

Gly Gly Gly Gly Ile Val Thr Leu Asp Ser Thr Leu Gly Asn Glu Phe
            420                 425                 430

Ser His Glu Val Gly His Asn Tyr Gly Leu Gly His Tyr Val Asp Gly
        435                 440                 445

Phe Lys Gly Ser Val His Arg Ser Ala Glu Asn Asn Asn Ser Thr Trp
    450                 455                 460

Gly Trp Asp Gly Asp Lys Lys Arg Phe Ile Pro Asn Phe Tyr Pro Ser
465                 470                 475                 480

Gln Thr Asn Glu Lys Ser Cys Leu Asn Asn Gln Cys Gln Glu Pro Phe
                485                 490                 495

Asp Gly His Lys Phe Gly Phe Asp Ala Met Ala Gly Gly Ser Pro Phe
            500                 505                 510

Ser Ala Ala Asn Arg Phe Thr Met Tyr Thr Pro Asn Ser Ser Ala Ile
        515                 520                 525

Ile Gln Arg Phe Phe Glu Asn Lys Ala Val Phe Asp Ser Arg Ser Ser
    530                 535                 540

Thr Gly Phe Ser Lys Trp Asn Ala Asp Thr Gln Glu Met Glu Pro Tyr
545                 550                 555                 560

Glu His Thr Ile Asp Arg Ala Glu Gln Ile Thr Ala Ser Val Asn Glu
```

```
                565                 570                 575
Leu Ser Glu Ser Lys Met Ala Glu Leu Met Ala Glu Tyr Ala Val Val
            580                 585                 590
Lys Val His Met Trp Asn Gly Asn Trp Thr Arg Asn Ile Tyr Ile Pro
        595                 600                 605
Thr Ala Ser Ala Asp Asn Arg Gly Ser Ile Leu Thr Ile Asn His Glu
    610                 615                 620
Ala Gly Tyr Asn Ser Tyr Leu Phe Ile Asn Gly Asp Glu Lys Val Val
625                 630                 635                 640
Ser Gln Gly Tyr Lys Lys Ser Phe Val Ser Asp Gly Gln Phe Trp Lys
                645                 650                 655
Glu Arg Asp Val Val Asp Thr Arg Glu Ala Arg Lys Pro Glu Gln Phe
            660                 665                 670
Gly Val Pro Val Thr Thr Leu Val Gly Tyr Tyr Asp Pro Glu Gly Thr
        675                 680                 685
Leu Ser Tyr Ile Tyr Pro Ala Met Tyr Gly Ala Tyr Gly Phe Thr
    690                 695                 700
Tyr Ser Asp Asp Ser Gln Asn Leu Ser Asp Asn Asp Cys Gln Leu Gln
705                 710                 715                 720
Val Asp Thr Lys Glu Gly Gln Leu Arg Phe Arg Leu Ala Asn His Arg
                725                 730                 735
Ala Asn Asn Thr Val Met Asn Lys Phe His Ile Asn Val Pro Thr Glu
            740                 745                 750
Ser Gln Pro Thr Gln Ala Thr Leu Val Cys Asn Asn Lys Ile Leu Asp
        755                 760                 765
Thr Lys Ser Leu Thr Pro Ala Pro Glu Gly Leu Thr Tyr Thr Val Asn
    770                 775                 780
Gly Gln Ala Leu Pro Ala Lys Glu Asn Glu Gly Cys Ile Val Ser Val
785                 790                 795                 800
Asn Ser Gly Lys Arg Tyr Cys Leu Pro Val Gly Gln Arg Ser Gly Tyr
                805                 810                 815
Ser Leu Pro Asp Trp Ile Val Gly Gln Glu Val Tyr Val Asp Ser Gly
            820                 825                 830
Ala Lys Ala Lys Val Leu Leu Ser Asp Trp Asp Asn Leu Ser Tyr Asn
        835                 840                 845
Arg Ile Gly Glu Phe Val Gly Asn Val Asn Pro Ala Asp Met Lys Lys
    850                 855                 860
Val Lys Ala Trp Asn Gly Gln Tyr Leu Asp Phe Ser Lys Pro Arg Ser
865                 870                 875                 880
Met Arg Val Val Tyr Lys
                885

<210> SEQ ID NO 3
<211> LENGTH: 11
<212> TYPE: PRT
<213> ORGANISM: Unknown Organism
<220> FEATURE:
<221> NAME/KEY: misc_feature
<223> OTHER INFORMATION: Description of Unknown Organism: E. coli O157:H7
      plasmid pO157

<400> SEQUENCE: 3

His Glu Val Gly His Asn Tyr Gly Leu Gly His
1               5                   10

<210> SEQ ID NO 4
```

-continued

```
<211> LENGTH: 28
<212> TYPE: DNA
<213> ORGANISM: Synthetic Oligonucleotide

<400> SEQUENCE: 4
ccctcgagtt tacgaaacag gtgtaaat                                    28

<210> SEQ ID NO 5
<211> LENGTH: 30
<212> TYPE: DNA
<213> ORGANISM: Synthetic Oligonucleotide

<400> SEQUENCE: 5
cctctagatt atttatatac aaccctcatt                                  30

<210> SEQ ID NO 6
<211> LENGTH: 30
<212> TYPE: DNA
<213> ORGANISM: Synthetic Oligonucleotide

<400> SEQUENCE: 6
ccgagctccg atgaaattaa agtatctgtc                                  30

<210> SEQ ID NO 7
<211> LENGTH: 27
<212> TYPE: DNA
<213> ORGANISM: Synthetic Oligonucleotide

<400> SEQUENCE: 7
cctcgagttt atatacaacc ctcattg                                     27

<210> SEQ ID NO 8
<211> LENGTH: 23
<212> TYPE: DNA
<213> ORGANISM: Synthetic Oligonucleotide

<400> SEQUENCE: 8
ccgctccggt gaactggaga ata                                         23

<210> SEQ ID NO 9
<211> LENGTH: 30
<212> TYPE: DNA
<213> ORGANISM: Synthetic Oligonucleotide

<400> SEQUENCE: 9
gaccataatt atgaccaaca tcatgactga                                  30

<210> SEQ ID NO 10
<211> LENGTH: 23
<212> TYPE: DNA
<213> ORGANISM: Synthetic Oligonucleotide

<400> SEQUENCE: 10
ccttatctgc ggaggctgta ggg                                         23

<210> SEQ ID NO 11
<211> LENGTH: 31
<212> TYPE: DNA
<213> ORGANISM: Synthetic Oligonucleotide

<400> SEQUENCE: 11
tgagttcagt catgatgttg gtcataatta t                                31
```

```
<210> SEQ ID NO 12
<211> LENGTH: 25
<212> TYPE: DNA
<213> ORGANISM: Synthetic Oligonucleotide

<400> SEQUENCE: 12
gagaataatc gaatcactta tgctc                                              25

<210> SEQ ID NO 13
<211> LENGTH: 21
<212> TYPE: DNA
<213> ORGANISM: Synthetic Oligonucleotide

<400> SEQUENCE: 13
cggtggagga acggctatcg a                                                  21

<210> SEQ ID NO 14
<211> LENGTH: 30
<212> TYPE: DNA
<213> ORGANISM: Synthetic Oligonucleotide

<400> SEQUENCE: 14
tttacgaaac aggtgtaaat atgttataaa                                         30

<210> SEQ ID NO 15
<211> LENGTH: 21
<212> TYPE: DNA
<213> ORGANISM: Synthetic Oligonucleotide

<400> SEQUENCE: 15
cagttcaccg gagcggaacc a                                                  21

<210> SEQ ID NO 16
<211> LENGTH: 25
<212> TYPE: DNA
<213> ORGANISM: Synthetic Oligonucleotide

<400> SEQUENCE: 16
gcttcagcaa gtggaatgca gatac                                              25

<210> SEQ ID NO 17
<211> LENGTH: 30
<212> TYPE: DNA
<213> ORGANISM: Synthetic Oligonucleotide

<400> SEQUENCE: 17
ttatttatat acaaccctca ttgacctagg                                         30
```

E. COLI O157:H7 C1 ESTERASE INHIBITOR-BINDING PROTEIN AND METHODS OF USE

CROSS-REFERENCE TO RELATED APPLICATION

This application claims priority to U.S. Provisional Application No. 60/243,675, filed Oct. 26, 2000.

STATEMENT REGARDING FEDERALLY SPONSORED RESEARCH OR DEVELOPMENT

This invention was made with United States government support awarded by NIH-A 120323.

BACKGROUND OF THE INVENTION

Enterohemorrhagic *Escherichia coli* (EHEC) serotype O157:H7 strain is a human enteric bacterial pathogen that causes diarrheal disease, hemorrhagic colitis, and hemolytic uremic syndrome (HUS). Each year in the United States, an estimated 20,000 people suffer from diarrheal disease associated with *E. coli* O157:H7 infection, which is typically contracted by ingesting contaminated foods, especially undercooked meat. Approximately 6% of infected individuals develop HUS, which can lead to renal failure and death. Young children and the elderly are particularly susceptible to developing HUS.

In general, bacterial infections are commonly treated by administering appropriate antibiotics. However, *E. coli* O157:H7 infection typically has a very rapid progression, and is consequently very difficult to treat. Often by the time the disease is diagnosed, the infected individual is severely ill and toxic proteins secreted by the bacteria may have damaged mucosal cells and entered the blood stream. Antibiotic treatment of patients infected with *E. coli* O157:H7 is generally not successful, and is now believed to be contraindicated.

*E. coli* O157:H7 bacteria are very proficient at establishing an infection; ingestion of as few as 10 live bacteria is sufficient to establish an infection. The highly infective nature of *E. coli* O157:H7 and the devastating sequelae associated with infection by this bacteria, together with the extensive public attention given to outbreaks of hemorrhagic colitis, has generated a great deal of interest among medical professionals and the general public in developing the means for early diagnosis and treatment of the disease. The entire genome of the *E. coli* O157:H7 EDL933W (ATCC 43895) was sequenced with the expectation that valuable information concerning the organism's pathogenicity would be uncovered, which may facilitate development of methods of preventing infections, or preventing or treating hemolytic uremic syndrome in individuals infected with of the organism. The DNA sequence of *E. coli* O157:H7 was compared with that of *E. coli* K12, a non-pathogenic strain commonly used in research. The genome of *E. coli* O157:H7 exceeds that of *E. coli* K-12 by more than a million base pairs and has up to 1000 genes not found on K-12. These additional gene sequences are distributed throughout more than 250 sites in islands, with each island containing from zero to sixty genes (1).

What is needed in the art is an improved understanding of factors involved in the pathogenesis of *E. coli* O157:H7, and methods for preventing or treating hemolytic uremic syndrome in individuals infected with *E. coli* O157:H7. What is also needed in the art is an understanding of factors responsible for enteric disease that are common to pathogenic *E. coli.*

BRIEF SUMMARY OF THE INVENTION

The present invention provides an isolated polypeptide comprising the amino acid sequence of amino acid residues 230–630 of SEQ ID NO:2.

In another aspect, the present invention provides an isolated polypeptide comprising an amino acid sequence having at least 70% amino acid identity to amino acid residues 24–886 of SEQ ID NO:2, the polypeptide comprising a sequence corresponding with and identical to amino acids 434–444 of SEQ ID NO:2 and having the ability to bind to and cleave C1 esterase inhibitor.

In another embodiment, the present invention provides an isolated polypeptide, the amino acid sequence of which comprises at least 17 consecutive amino acid residues of SEQ ID NO:2.

In yet another aspect, the present invention provides a genetic construct comprising a polynucleotide encoding a polypeptide comprising the amino acid sequence of amino acid residues 24–886 of SEQ ID NO:2 or a sequence complementary thereto, the polynucleotide operably linked to an expression control sequence. Additionally, the present invention is drawn to a cell comprising the genetic construct.

In another embodiment, the present invention includes an antibody that binds specifically to an antigenic determinant found on a polypeptide comprising an amino acid sequence comprising SEQ ID NO:2, preferably to an epitope in the C1 esterase inhibitor binding domain of the polypeptide.

In another aspect, the present invention provides a method of preventing or treating colitis or hemolytic uremic syndrome in a subject infected with an enterohemorrhagic pathogen expressing an inhibitor protein comprising an amino acid sequence substantially homologous to SEQ ID NO:2, the inhibitor protein being capable of reducing the activity of C1 esterase inhibitor, comprising administering to the subject an antibody that binds specifically to an antigenic determinant found on a polypeptide having the amino acid sequence of SEQ ID NO:2, or a chelator capable of binding divalent cations, the antibody or chelator administered in an amount effective to reduce proteolytic inactivation of C1 esterase inhibitor by the inhibitor protein.

Another aspect of the invention provides a method of preventing colitis or hemolytic uremic syndrome in a subject at risk for infection with an enterohemorrhagic pathogen expressing an inhibitor protein comprising an amino acid sequence substantially homologous to SEQ ID NO:2, the inhibitor protein being capable of reducing the activity of C1 esterase inhibitor, comprising administering to the subject an inactivated polypeptide comprising at least one antigenic determinant of a polypeptide comprising the amino acid sequence of SEQ ID NO:2 in an amount effective to induce an immune response.

In another aspect, the invention provides a method of preventing or treating colitis and/or hemolytic uremic syndrome in a subject infected with an enterohemorrhagic pathogen expressing an inhibitor protein comprising an amino acid sequence substantially homologous to SEQ ID NO:2, the protein inhibitor being capable of reducing the activity of C1 esterase inhibitor, comprising the step of administering to the subject C1 esterase inhibitor in an amount effective to reduce activation of at least one proteolytic cascade selected from the group consisting of classical complement cascade, intrinsic coagulation pathway, and kinin-forming system.

The present invention provides a method of testing a molecule for the ability to reduce proteolysis of C1 esterase inhibitor by an inhibitor protein comprising an amino acid sequence substantially homologous to amino acid residues 24 to 886 of SEQ ID NO:2, the inhibitor protein being capable of proteolyzing C1 esterase inhibitor, comprising combining the inhibitor protein, test molecule, and C1 esterase inhibitor under suitable conditions for a period of time sufficient to allow inhibitor protein-C1 esterase inhibitor interaction; and comparing the level of the C1 esterase inhibitor or C1 esterase inhibitor activity to that of a control lacking the test molecule.

BRIEF DESCRIPTION OF THE SEVERAL VIEWS OF THE DRAWINGS

FIG. 6 shows differential cleavage of C1-INH by StcE and elastase.

DETAILED DESCRIPTION OF THE INVENTION

Figure 1:
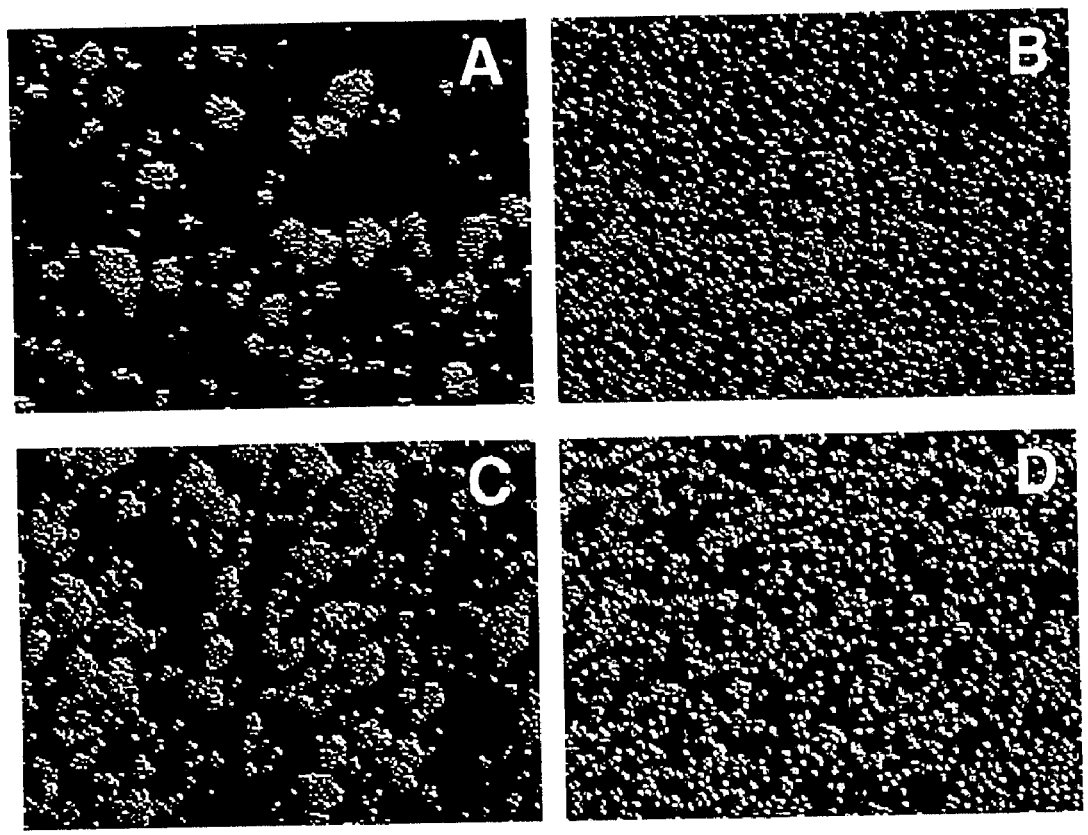
FIG. 1 shows the differential effect of *E. coli* strains containing (FIG. 1A and FIG. 1C) or lacking (FIG. 1B and FIG. 1D) the plasmid pO157 on aggregation of T cells.

Strains of the serotype O157:H7 EDL933W carry a 92 kb plasmid designated pO157. As described in the Examples below, bacterial strains containing the plasmid cause the aggregation of two cultured human CD4+ T cell lines, Jurkat and MOLT-4, but not a B cell lymphoma line (Raji), or macrophage-like cell lines (U937 and HL-60). Aggregation of the cells occurs in the presence of serum, but not in the absence of serum. Strains lacking the plasmid do not cause aggregation. We employed transposon mutagenesis to identify a gene on pO157 of previously unknown function whose product is associated with the observed aggregation effect. The coding sequence and the deduced amino acid sequence of the protein it encodes are shown in SEQ ID NO:1 and SEQ ID NO:2, respectively. The protein, designated "StcE", contains a putative cleavable N-terminal signal sequence, is secreted into the culture medium, and is a protease that cleaves C1 esterase inhibitor, a protease inhibitor that controls the activation of C1, the first component of the complement cascade.

As one of skill in the art would appreciate, a protein comprising an amino acid sequence having minor substitutions, deletions, or additions from that of SEQ ID NO:2 would be suitable in the practice of the present invention. Conservative amino acid substitutions are unlikely to perturb the protein's secondary structure and interfere with its activity. SEQ ID NO:2 includes the N-terminal signal sequence, which although expressed, is unlikely to be found on an isolated polypeptide. The expressed StcE protein likely undergoes post translational modification that results in cleavage of the N-terminal signal peptide. It is likely that StcE isolated from culture medium in which stcE positive strains are grown comprises amino acid residues 24–886 of SEQ ID NO:2. As shown in the Examples below, it appears that the 5' region of the StcE gene and promoter is less highly conserved than the 3' region of the gene.

It is specifically envisioned that isolated polypeptides having less than the full length sequence of amino acid residues 24–886 of SEQ ID NOL:2 will be useful in the practice of the present invention. StcE polypeptides that are truncated at the N-terminal or C-terminal regions and but have an intact metalloprotease binding domain corresponding to amino acid residues 434–444 of SEQ ID NO:2 may retain the ability to bind to and/or cleave the C1 esterase inhibitor. Binding and proteolytic activity of polypeptides can be evaluated using the methods set forth herein in the Examples, or by any suitable method. It is expected that StcE polypeptides that are truncated at the N-terminal or C-terminal regions or a polypeptide comprising an amino acid sequence comprising at least 17 consecutive amino acid residues of SEQ ID NO:2 may be used as an antigen against which antibodies specific for StcE may be raised. Preferably, the polypeptide comprises at least 25 consecutive amino acid residues of SEQ ID NO:2. More preferably still, the polypeptide comprises at least 40 consecutive amino acid residues of SEQ ID NO:2. One of ordinary skill in the art could easily obtain any of the various polypeptides comprising a portion of SEQ ID NO:2 by subcloning a sequence encoding the polypeptide into an expression vector, introducing the expression vector into a suitable host cell, culturing the cell, and isolating the expressed polypeptide using standard molecular biological techniques.

As used herein, an "inhibitor protein" is a polypeptide having substantial sequence identity with amino acid residues 24 to 886 of SEQ ID NO:2. As used herein, an inhibitor protein with substantial sequence identity to amino acid residues 24 to 886 of SEQ ID NO:2 comprises an amino acid sequence that has at least 70% amino acid identity to amino acid residues 24 to 886 of SEQ ID NO:2 and which has inhibitor protein activity. As used herein, "inhibitor protein activity" includes the ability to bind to C1 esterase inhibitor, proteolyze C1 esterase inhibitor, and promote T cell aggregation in the presence of C1 esterase inhibitor. More preferably, an inhibitor protein of the present invention has 90% amino acid identity with amino acid residues 24–886 of SEQ ID NO:2; most preferably still, an inhibitor protein of the present invention has 95% amino acid identity with amino acid residues 24–886 of SEQ ID NO:2.

By an "isolated polypeptide" is meant a polypeptide that has been at least partially purified from contaminants and which is found other than in its natural state. For example, a isolated polypeptide could be obtained from a fecal sample by filtering the sample. One may obtain an isolated polypeptide using any partial purification of the polypeptide from the supernatant of a culture of bacterium that secrete the polypeptide, or from a bacterial cell lysate of bacteria that express but the polypeptide but do not secrete it.

In the examples below, polyclonal antibodies were raised against StcE protein in a band excised from a polyacrylamide gel. These antibodies were found to bind specifically to StcE protein. An antibody that binds specifically to an antigenic determinant is one that binds to a protein corresponding to a polypeptide comprising the amino acid sequence of amino acid residues 24–886 of SEQ ID NO:2, or to peptide fragments thereof, but does not bind significantly to other proteins. One of skill in the art will appreciate that using standard methods, one could raise monoclonal antibodies to a polypeptide comprising the amino acid sequence of amino acid residues 24–886 of SEQ ID NO:2 or peptide fragments, and that the monoclonal antibodies would also be useful in the practice of the present invention.

It is envisioned that an antibody preparation comprising at least one antibody directed against any of the antigenic determinants of the polypeptide of amino acid residue 24–886 could be used to passively immunize a person against a bacterium expressing a StcE protein. Preferably, the antibody preparation comprises an antibody that binds in the region of amino acid residues 434–444 of SEQ ID NO:2.

Because the StcE protein is a metalloprotease that requires zinc for its activity, it is envisioned that infections with bacteria expressing StcE or a related protein may be treated by delivering an agent capable of binding to a divalent cation in an amount effective in preventing or treating colitis or hemolytic uremic syndrome in a patient infected with an enterohemorrhagic pathogen expressing an inhibitor protein having substantial sequence identity to amino acid residues 24–886 of SEQ ID NO:2. Examples of suitable chelators include, without limitation, EDTA, meso-2,3-dimercaptosuccinic acid (DMSA), bathophenanthroline-disulfonic acid (BPS), and penicillamine. The amount of each agent effective to inhibit StcE activity will, of course, depend on a variety of factors, including the age, sex, and weight of the individual, for example. To treat other conditions, EDTA has been administered at a rate of 2–3 grams per person over 3 hours. DMSA, which can chelate copper, manganese, molybdenum, and zinc, as well as lead, mercury, cadmium, and arsenic, has been administered for treating heavy metal toxicity, and may be taken orally. Typical dosage protocols range from 500 mg/day every other day for a minimum of 5 weeks to 10–30 mg/kg/day using a three-days-on, 11-days-off cycle for a minimum of 8 cycles. However, it is expected that shorter periods of treatment may be indicated. Penicillamine, another chelator primarily used to treat arthritis, can chelate copper, iron, and zinc. It is expected that dosages in the range of 125–750 mg/day may be effective.

It is also expected that the adverse effects that derive from the proteolytic activity of StcE inhibitor protein may be counteracted by administering to the patient C1-INH in an effective amount. To treat acute attacks of hereditary angioedema (HAE), as little as 25 U/kg has been given to patients (2). For other diseases, initial doses range vary from about 60 U/kg intravenously (i.v.) for patients with vascular leak syndrome to about 6000 U/kg i.v. for patients with severe thermal injury with septic shock. These initial doses can be followed by repeated administration of C1-INH over several days, if necessary. A regimen including an initial dose of 2000–4000 U/kg i.v., followed by additional C1-INH injections (e.g., 1000 U/kg i.v. daily for four days, and variations thereof) has been used to treat septic shock (3). C1-INH can be obtained commercially from various vendors (e.g., Cortex Biochem), or can prepared from pooled human plasma by a variety of protocols (2) (4).

As described below in the examples, the stcE ORF was amplified by PCR, the PCR product comprising the stcE ORF was functionally inserted into an expression vector, the recombinant vector was introduced into a bacterial host, and the bacterial host was cultured under conditions suitable for expression of the StcE protein. The StcE protein was purified and characterized as described below in the examples. The above described method of expressing and isolating StcE is a preferred method of obtaining an inhibitor protein of the present invention. However, as one of ordinary skill in the art will appreciate, the protein may be isolated from any other source, including, for example, from culture medium in which bacteria harboring the pO157 plasmid are grown.

The ability of an isolated polypeptide to bind C1-INH or cleave C1-INH may be assessed using any suitable method, including those methods described in detail in the examples below.

In order to evaluate the StcE protein for possible cytotoxic effects, a variety of cell types were treated with StcE protein as described in the examples. Cells treated with StcE showed a high degree of aggregation in the presence of serum, but not in the absence of serum.

Because StcE-mediated aggregation occurred only in cells also treated with serum, the ability of StcE to bind to a specific serum protein was evaluated by Far western blotting using the StcE protein as the probe. An acidic serum protein of about 105 kDa by SDS PAGE was identified as binding to StcE. The target protein was recovered, subjected to limited digestion by an endopeptidase, and the peptide products analyzed by mass spectrometry. The protein to which the StcE protein binds was identified as C1 esterase inhibitor (C1-INH), which serves as a critical inhibitor in the proteolytic cascade involved in complement activation.

The plasma protein C1-INH is a protease inhibitor that controls the activation of C1, the first component of the complement cascade. The C1 component is made up of three subcomponents: C1q, C1r, and C1s. In the classical pathway of complement activation, C1 binds to an antigen-antibody complex or certain pathogens (e.g., HIV-1) which causes the proteolytic autoactivation of C1r, which in turn causes the proteolytic activation of C1s. C1-INH inhibits activation of the classical pathway by binding to C1 and inactivating C1r and C1s. In addition to its role in controlling activation of the classical complement pathway, C1-INH inhibits other serine proteases involved in the intrinsic coagulation pathway and kinin-forming system (reviewed in (3)).

Treatment of serum or purified C1-INH with purified StcE results in the apparent disappearance of C1-INH, putatively as a result of specific proteolytic cleavage of C1-INH by StcE. The predicted StcE amino acid sequence comprises the sequence HEVGHNYGLGH (SEQ ID NO:3) (residues 434–444 of SEQ ID NO:2), which corresponds to the histidine rich active site of metalloproteases (5). Further evidence that StcE may be a metalloprotease is provided by the observation that proteolysis of C1-INH by StcE is reduced in the presence of EDTA or BPS, which chelate divalent metal ions (e.g., $Zn^{2+}$) required for metalloprotease activity.

Deficiencies in C1-INH can lead to a variety of diseases. For example, a hereditary deficiency in C1-INH (hereditary angiodema) is characterized by transient, recurrent attacks of intestinal cramps, vomiting and diarrhea. Hereditary defects in production of a different inhibitor of the complement cascade, Factor H, are associated with a form of hemolytic uremic syndrome (HUS) similar to that described for EHEC-mediated HUS.

Secretion of the putative protease StcE by enterohemorrhagic strains of *E. coli* EHEC may lead to proteolysis of C1-INH and reduction of C1-INH activity. Loss of C1-INH activity may result in unregulated pro-inflammatory or coagulation response that may be responsible for tissue damage in the intestine and kidney of persons infected with EHEC. It is also possible that the StcE serum-dependent cellular aggregation phenotype plays a role in the pathogenesis of HUS because one of the hallmarks of HUS is thrombocytopenia with an accumulation of a large number of platelets in renal microthrombi. The kidneys of those diagnosed with HUS also contain large amounts of deposited fibrin.

The proteolytic activity of StcE may be a common mode of pathogenesis among some diarrheagenic strains of *E. coli*. Colony blot analysis and amplification of *E. coli* DNA using oligomers specific to the pO157 version of stcE indicate that the stcE gene is common to all tested strains of *E. coli* associated with bloody colitis and HUS, but the stcE gene is not present in enteroinvasive, enterotoxigenic or uropathogenic strains of *E. coli*. However, some closely related strains of enteropathogenic *E. coli* contain stcE, which suggests that StcE may be more widely distributed among diarrheagenic *E. coli* than appreciated initially. Additionally, a search of the GenBank database has identified at least one distant homolog to StcE: a Vibrio cholerae protein (designated TagA) of unknown function. We can envision a method to screen for similar virulence factors produced by microbes.

StcE interacts with and cleaves the human serum protein complement C1 inhibitor in a zinc-dependent manner. Inactivation of serine protease inhibitors by this type of virulence factor may result in an unregulated pro-inflammatory and coagulation response that may be responsible for tissue damage in the intestine and kidney in patients infected with enterohemorrhagic strains of *E. coli*.

The elucidation of StcE functions may result in new targets for chemotherapeutic or immune-based prevention or treatment of EHEC diseases. Active or passive immune prophylaxis using StcE as an antigen or anti-StcE antibodies may prevent the serious sequalae associated with infections by enterohemorrhagic *E. coli*. Identification of the active site or binding sites between StcE and C1-INH may facilitate the design of drugs capable of preventing proteolysis of C 1-INH and the tissue damage that results as a consequence of the loss of C1-INH activity. Administration of C1-INH to patients suffering from hereditary angiodema is a common practice (6). We envision that administration of C 1-INH could be an effective therapy for patients suffering from bloody colitis, HUS or thrombotic thrombocytopenic purpura (TTP).

The following non-limiting examples are intended to be purely illustrative.

EXAMPLES

Bacterial strains and plasmids.

A list of bacterial strains and plasmids is found in Table 1. Strains were constructed and plasmids were maintained in either *E. coli* K-12 DH1 or C600 unless otherwise noted. Recombinant DNA manipulations were performed by standard methods.

Enterohemorrhagic *Escherichia coli* strains EDL933 and EDL933cu (lacking plasmid pO157) and WAM2371 (enteropathogenic *E. coli* strain E2348/69) were provided by Dr. Alison O'Brien of the Uniformed Services University. WAM2035 (C600/pO157) was provided by Dr. Hank Lockman of the Uniformed Services University. WAM2516 (*Citrobacter rodentium* strain DBS100) was provided by Dr. David Schauer of the Massachusetts Institute of Technology. The Diarrheagenic *E.coli* (DEC) collection was a gift from Dr. Tom Whittam of the University of Pennsylvania. WAM2547 was created by transforming pLOF/Km (a gift from Dr. Victor De Lorenzo of the GBF-National Research Centre for Biotechnology, Germany) into the donor strain S17($\lambda$pir).

TABLE 1

Bacterial strains and plasmids used in this study.

| Strain | Relevant phenotype or plasmid genotype | Source |
|---|---|---|
| C600 | *E. coli* K-12 | this laboratory |
| DH1 | laboratory strain of *E. coli* | this laboratory |
| S17($\lambda$pir) | *E. coli* donor strain for conjugation | this laboratory |
| BL21(DE3) | *E. coli* strain for protein overexpression | Novagen |
| EDL933 | wild-type EHEC strain | A. O'Brien |
| EDL933cu | EHEC strain EDL933 cured of pO157 | A. O'Brien |
| WAM2371 | EPEC strain E2348/69 | A. O'Brien |
| WAM2516 | *C. rodentium* strain DBS100 | D. Schauer |
| DEC strains | Diarrheagenic *E. coli* collection | T. Whittam |
| WAM2035 | C600/pO157::Tn801 (amp$^r$) | H. Lockman |
| WAM2515 | C600/pO157::Tn801 (amp$^r$ nal$^r$) | this study |
| WAM2297 | DH1/pBluescript II SK+ (amp$^r$) | this laboratory |
| WAM2547 | S17($\lambda$pir)/pLOF/Km (amp$^r$ kan$^r$) | this study |
| WAM2553 | C600/pWL104 (amp$^r$ kan$^r$) | this study |
| WAM2562 | DH1/pWL105 (amp$^r$) | this study |
| WAM2572 | BL21(DE3)/pWL107 (kan$^r$) | this study |
| WAM2726 | BL21(DE3)/pTEG1 (kan$^r$) | this study |
| pLOF/Km | pGP704 carrying miniTn10kan | V. De Lorenzo |
| pO157 | 92 kb plasmid of EDL933; Tn801 at base 5413 | H. Lockman |
| pBluescript II SK+ | cloning vector | Stratagene |
| pET24d(+) | 6xHis overexpression vector | Novagen |
| pWL104 | pO157::miniTn10kan inserted at base 23772 | this study |
| pWL105 | pBluescript II SK+/bases 1–2798 of L7031 | this study |
| pWL107 | pET24d(+)/bases 138–2795 of L7031 | this study |
| pTEG1 | pWL107 with amino acid change E435D | this study |

WAM2515 is a spontaneous nalidixic acid-resistant mutant of WAM2035. WAM2553 was created as described below, containing a mini-Tn10kan insertion at base 23772 of pO157 (accession #AF074613). This plasmid is designated pWL104. WAM2297 is pBluescript II SK+in DH1. pWL105 was constructed by amplifying bases 1 to 2798 of the promoter and gene L7031/stcE from pO157 by polymerase chain reaction (PCR) using primer pairs 5'-CCCTCGAGTTTACGAAACAGGTGTAAAT-3' (SEQ ID NO:4) and 5'-CCTCTAGATTATTTATATACAACCCTCATT-3' (SEQ ID NO: 5); and cloning the product into the XbaI-XhoI sites of pBluescript II SK+(Stratagene); WAM2562 is DH1 containing pWL105. pWL107 was constructed by PCR amplification of bases 138 to 2798 of the promoter and gene L7031/stcE from pO157 by PCR using primer pairs 5'-CCGAGCTCCGATGAAATTAAAGTATCTGTC-3' (SEQ ID NO:6) and 5'-CCTCGAGTTTATATACAACCCTCATTG-3' (SEQ ID NO:7); and cloning the PCR product into the SacI-XhoI sites of pET-24d(+) (Novagen); WAM2572 is BL21(DE3) (Novagen) transformed with pWL107. The creation of WAM2726 is described below. All chemicals were purchased from Sigma (St. Louis, Mo.) unless stated otherwise.

Cell Lines

All cell lines were maintained in RPMI 1640 medium (Gibco) supplemented with 10% fetal bovine serum (HyClone) and 10 $\mu$g/ml gentamicin at 37° C. with 5% $CO_2$.

The human T cell line Jurkat clone E6-1, the human promyelocytic leukemia line HL-60, and the human B cell lymphoma line Raji were obtained from ATCC, the human promyelocytic leukemia line U937 was a gift from Dr. Jon Woods of the University of Wisconsin-Madison, and the human T cell lymphoma line MOLT-4 was a gift from Dr. David Pauza of the University of Wisconsin-Madison.

Aggregation Assays.

Bacterial strains were grown overnight in Lennox L broth (with antibiotic selection when appropriate) at 37° C. with agitation. Cultures were washed once with phosphate buffered saline (PBS) and resuspended in $\frac{1}{10}$ the original culture volume in PBS. Cultures were lysed in a French Press at 20,000 lbs/in$^2$. The resulting lysates were spun at 1000×g to remove debris and protein concentrations were determined by the Bradford protein assay (Bio-Rad). Tissue culture cells were suspended at 10$^6$ cells/ml in RPMI 1640 and 50 µg/ml gentamicin with 10% FBS or human serum. Fifty µg/ml of lysates or 50–200 ng/ml purified StcE-His (see below) were added to cells and incubated for two hours at 37° C. in 5% $CO_2$. Cells were agitated for one minute to disrupt spontaneous aggregates before visualization. Similar assays were performed in the absence of serum or with ammonium sulfate-precipitated fractions of human serum (see below); cells were washed once in RPMI 1640 and resuspended at 1×10$^6$ cells/ml in RPMI 1640 with 50 µg/ml gentamicin (and human serum fractions, if indicated) before the addition of lysates or StcE-His. When indicated, ethylenediaminetetraacetic acid (EDTA) or bathophenanthroline-disulfonic acid (BPS) were added to the assays at a final concentration of 5 mM.

Identification of StcE

WAM2515 was mated with WAM2547 as described (7). Transconjugants were plated onto LB plates containing 100 µg/ml ampicillin, 50 µg/ml kanamycin, and 50 µg/ml nalidixic acid. Transconjugants were resuspended in 1×TES, washed once with 1×TES, and pO157/pO157::mini-Tn10kan were isolated by midi-prep (Qiagen). pO157/pO157::mini-Tn10kan were transformed into C600 and plated onto LB plates containing 100 µg/ml ampicillin and 50 µg/ml kanamycin. Transformants were grown overnight in Lennox L broth containing 100 µg/ml ampicillin and 50 µg/ml kanamycin at 37° C. with agitation and lysates were screened for the ability to aggregate Jurkat cells as described above. pO157::mini-Tn10kan was isolated from clones lacking the ability to aggregate Jurkat cells and the location of the transposable element was identified by sequence analysis. One clone unable to aggregate Jurkat cells was designated WAM2553.

Purification of Recombinant StcE-His

StcE-His was purified according to the manufacturer's instructions (Novagen). Briefly, WAM2572 was induced to produce StcE-His by the addition of IPTG to 1 mM at an O.D. of 0.5 followed by vigorous aeration at 37° C. for approximately three hours. The cells were lysed in a French Press at 20,000 lbs/in$^2$ and the resulting lysate was centrifuged at 20,000×g for 15 minutes. The insoluble pellet was resuspended in a buffer containing 5 mM imidazole and 6 M urea and the inclusion bodies were solubilized for one hour on ice. This fraction was incubated with nickel-agarose beads (Qiagen) overnight at 4° C., and the beads were washed three times with a buffer containing 60 mM imidazole and 6 M urea. Purified StcE-His was eluted from the beads with a buffer containing 300 mM imidazole and 6 M urea. Eluted StcE-His was dialyzed against three changes of PBS/20% glycerol at 4° C. to remove the imidazole and urea. Protein concentration was determined by SDS-PAGE using purified β-galactosidase as a standard. At our request, polyclonal antibodies to purified StcE-His were prepared in rabbits by Cocalico Biologicals, Inc. Briefly, purified StcE-His was electrophoresed on an 8% polyacrylamide gel and stained with Coomassie Brilliant Blue. StcE-His was excised from the gel and injected into rabbits. Rabbits were boosted with StcE-His once a month for six months prior to exsanguinations.

Two-dimensional Gel Electrophoresis

Human serum was fractionated by ammonium sulfate precipitation, dialyzed against three changes of RPMI 1640 (Gibco) overnight at 4° C., and protein concentration was determined by Bradford assay (Bio-Rad). When indicated, protein A-sepharose was used to remove fractions of IgG. Two-dimensional electrophoresis was performed according to the method of O'Farrell (8) by Kendrick Labs, Inc. (Madison, Wis.) as follows: isoelectric focusing was carried out on 25 µg of 30–60% ammonium sulfate-fractionated human serum removed of IgG in glass tubes of inner diameter 2.0 mm using 2.0% pH 3.5–10 ampholines (Amersham Pharmacia Biotech) for 9600 volt-hrs. Fifty ng of an IEF internal standard, tropomyosin, was added to each sample. This protein migrates as a doublet with lower polypeptide spot of MW 33,000 and pI 5.2; an arrow on the stained gel marks its position. The enclosed tube gel pH gradient plot for this set of ampholines was determined with a surface pH electrode.

After equilibration for 10 min in buffer "0" (10% glycerol, 50 mM dithiothreitol, 2.3% SDS and 0.0625 M Tris, pH 6.8) each tube gel was sealed to the top of a stacking gel that is loaded on the top of a 8% acrylamide slab gel (0.75 mm thick). SDS slab gel electrophoresis was carried out for about 4 hrs at 12.5 mA/gel. The following proteins (Sigma) were added as molecular weight standards to a well in the agarose which sealed the tube gel to the slab gel: myosin (220 kDa), phosphorylase A (94 kDa), catalase (60 kDa), actin (43 kDa), carbonic anhydrase (29 kDa), and lysozyme (14 kDa). These standards appear as bands on the basic edge of the special silver-stained (O'Connell and Stults 1997) 8% acrylamide slab gel. The gel was dried between sheets of cellophane with the acidic edge to the left.

A similar gel was run as described above with the following differences: 250 µg of 30–60% ammonium sulfate-fractionated human serum was loaded onto the IEF gel; the second dimension was run on a 10% acrylamide slab gel and stained with Coomassie Brilliant Blue.

Far Western Blot Analysis

One hundred µg of 30–60% ammonium sulfate-fractionated human serum was run on a two-dimensional gel as described above but without staining. After slab gel electrophoresis the gel for blotting was transferred to transfer buffer (12.5 mM Tris, pH 8.8, 86 mM glycine, 10% methanol) and transblotted to PVDF membrane overnight at 200 mA and approximately 50 volts/gel. The PVDF membrane was blocked with 2% milk (Difco) in buffer AD (20 mM Tris, pH 7.5, 100 mM NaCl, 10% glycerol, 0.01% Tween-20) at 4° C. Two µg/ml purified StcE-His was added to the PVDF membrane and allowed to incubate two hours at 4° C. The membrane was washed with buffer AD and blocked with 2% milk in buffer AD. The membrane was reacted with polyclonal anti-His antibody conjugated with horse-radish peroxidase (Santa Cruz), washed with buffer AD, and developed with the LumiGlo chemiluminescence detection system (Kirkegaard & Perry Laboratories). The PVDF membrane was then stripped (62 mM Tris, pH 6.8, 2% SDS, 10 mM β-mercaptoethanol (β-ME), 30 min, 50° C.), washed with buffer AD, reacted as above with only the His-HRP antibody, and developed.

Mass Spectrometry

Of the three spots in human serum that reacted with purified StcE-His as identified by Far Western blotting, only the leftmost spot (the most acidic) of approximately 100 kDa was accessible for analysis by mass spectrometry. This spot was cut from the Coomassie Brilliant Blue-stained 10% slab gel and sent to the Protein Chemistry Core Facility at the Howard Hughes Medical Institute/Columbia University for analysis. The spot was digested with endoproteinase Lys-C and analyzed by MALDI-MS. The peptide pattern was compared against known human proteins in the SWISS-PROT database and was identified as plasma protease C1 inhibitor.

Electrophoresis and Immunoblot Analyses

Fifty $\mu$g whole and ammonium sulfate-precipitated human serum fractions were incubated with 500 ng purified StcE-His in 500 $\mu$l buffer AD for two hours at room temperature and precipitated with 10% trichloroacetic acid (TCA) on ice for one hour. Precipitates were collected by centrifugation, resuspended in 1× sample buffer (2% SDS, 10% glycerol, 5% β-ME, 1 mM bromophenol blue, 62 mM Tris, pH 6.8), and heated to 95–100° C. for 5 min prior to electrophoresis on 8% polyacrylamide gels. Separated proteins were transferred to Hybond ECL nitrocellulose (Amersham Pharmacia Biotech) as described (9) for immunoblot analysis. Blots were blocked with 5% milk in TBST (154 mM NaCl, 20 mM Tris, pH 7.6, 0.1% Tween-20), probed with a polyclonal anti-C1 inhibitor antibody (Serotec) and then with HRP-conjugated anti-rabbit secondary antibody (Bio-Rad) before developing as described above.

Sixteen $\mu$g purified C1 inhibitor (Cortex Biochem) were incubated with 4.8 $\mu$g purified StcE-His in 480 $\mu$l buffer AD at room temperature; 30 $\mu$l of the reaction were removed at various time points, suspended in 1× sample buffer, and heated to 95–100° C. for 5 min prior to electrophoresis on 8% polyacrylamide gels. Separated proteins were transferred to nitrocellulose and reacted with anti-C1 inhibitor antibody as described above.

EDL933, EDL933cu, WAM2035, and WAM2553 were grown in Lennox L broth at 37° C. overnight, centrifuged, and the culture supernatant was removed. The supernatant was precipitated with ammonium sulfate and the 0–60% fraction was resuspended at ¹⁄₁₀₀ the original culture volume and dialyzed against three changes of PBS overnight at 4° C. Twenty $\mu$l of the dialyzed supernatants and 30 $\mu$g of EDL933, EDL933cu, WAM2035, and WAM2553 lysates were suspended in 1× sample buffer and heated to 95–100° C. for 5 min prior to electrophoresis on 8% polyacrylamide gels. Separated proteins were transferred to Hybond ECL nitrocellulose and reacted with polyclonal anti-StcE-His antibody, followed by anti-rabbit-HRP secondary antibody.

Casein Proteolysis Assay

Various concentrations of StcE-His were incubated with BODIPY FL-conjugated casein for various times using the EnzChek Protease Assay Kit (Molecular Probes, Inc.) and the increase in fluorescence was measured with a fluorimeter as per the manufacturer's instructions.

Lysates of E. coli Strains Carrying pO157 Induce the Aggregation of Transformed Human T Cell Lines in a Serum-dependent Manner.

To determine the consequence of pO157-containing E. coli products on Jurkat cells, a human T cell lymphoma line, 50 $\mu$g/ml of lysates of strains EDL933, EDL933cu, WAM2035, WAM2371, WAM2516, and C600 were applied to 1×10⁶ Jurkat cells/ml in RPMI 1640 with 10% FBS and 50 $\mu$g/ml gentamicin for two hours at 37° C. in 5% $CO_2$. After agitation for one minute to disrupt spontaneous aggregates, Jurkats were observed for the induction of aggregation. Lysates of E. coli strains carrying pO157 induced the aggregation of Jurkat cells while lysates of strains lacking pO157 did not (FIG. 1). Lysates of other pathogenic bacteria such as enteropathogenic E. coli strain E2348/69 (WAM2371) and C. rodentium (WAM2516) capable of inducing the attaching and effacing (A/E) phenotype on intestinal epithelial cells and carrying large virulence plasmids different from pO157 were unable to induce the aggregation of Jurkat cells. To determine whether this effect was specific for Jurkat cells or could induce the aggregation of a broader host cell range, 1×10⁶ cells/ml in RPMI 1640 with 10% FBS and 50 $\mu$g/ml gentamicin of another human T cell lymphoma line, MOLT-4, two human promyelocytic leukemia cell lines, HL-60 and U937, and a human B cell lymphoma line, Raji, were treated with 50 $\mu$g/ml of EDL933 and WAM2035 lysates for two hours at 37° C. in 5% $CO_2$. pO157-containing lysates aggregated MOLT-4 cells but not HL-60, U937, or Raji cells (data not shown), indicating T cell specificity for the phenotype.

To determine the serum requirement for the induction of aggregation, 50 $\mu$g/ml of lysates of EDL933 and WAM2035 were applied to 1×10⁶ Jurkat cells/ml with 10% human serum and 50 $\mu$g/ml gentamicin for two hours at 37° C. in 5% $CO_2$. As seen with FBS, pO157-containing lysates were able to induce the aggregation of Jurkat cells in the presence of human serum. However, EDL933 and WAM2035 lysates were unable to induce the aggregation of Jurkat cells under the same conditions in the absence of serum. To further characterize the component(s) of human serum responsible for mediating Jurkat cell aggregation in the presence of StcE, we fractionated human serum by ammonium sulfate precipitation followed by dialysis in RPMI 1640. We found that 0–30% and 30–60%, but not 60–100%, ammonium sulfate-precipitated human serum was able to mediate aggregation of Jurkat cells in the presence of StcE. This indicates a factor or factors in serum is required for the aggregation of Jurkat cells when treated with lysates of pO157-containing bacteria.

Identification and Cloning of StcE

To localize the gene(s) on pO157 responsible for the induction of aggregation of human T cell lines, we subjected pO157 to mutagenesis using a minitransposon. Lysates of recombinant strains of E. coli containing pO157 mutagenized with mini-Tn10kan were tested for the ability to aggregate Jurkat cells in RPMI 1640 with 10% FBS and 50 $\mu$g/ml gentamicin. pO157::mini-Tn10kan was isolated from clones whose lysates were unable to induce the aggregation of Jurkat cells. The location of the transposon insertion in WAM2553 was determined by sequence analysis and mapped to position 23772 of pO157. The open reading frame in which the transposon inserted was designated L7031 (10) and is located immediately 5' to the general secretory apparatus on pO157. L7031/stcE was amplified and cloned into the XbaI-XhoI sites of pBluescript II SK+. Lysates of WAM2562 induced aggregation of Jurkat cells in the presence of serum, whereas lysates of WAM2297 (DH1 carrying pBluescript II SK+) did not, which confirms that the stcE gene is responsible for the phenotype.

Based on sequence analysis, we concluded that the translational start site for StcE was more likely to begin at base 138 than at base 102 (10). We therefore amplified the coding sequence for stcE from bases 138 to 2798 by PCR and cloned the gene in frame with a 6xHis-tag at the 3' end of the fusion in pET24d(+). We were able to overexpress and purify a recombinant his-tagged form of StcE (StcE-His)

Figure 2:
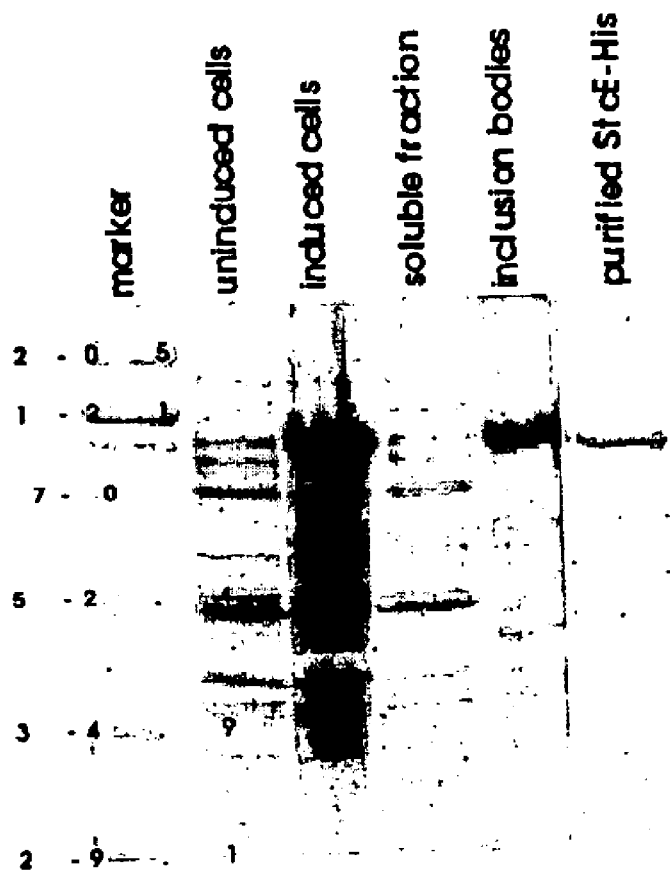
FIG. 2 shows stained proteins separated by SDS/PAGE.

(FIG. 2); this purified fusion protein was able to aggregate Jurkat cells in the presence of serum at a variety of concentrations (data not shown).

Localization and Characterization of StcE

Figure 3:
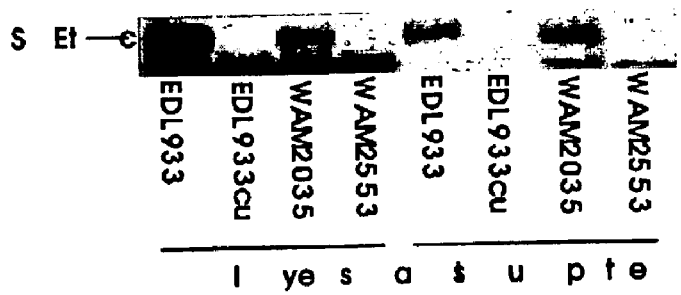
FIG. 3 shows that synthesis of StcE correlates with the presence of pO157.

Using antiserum to StcE-His, we performed immunoblot analysis to examine the expression and secretion of StcE by *E. coli*. StcE is expressed by *E. coli* strains carrying pO157 at 37° C. in Lennox L broth but not in strains lacking pO157 or harboring a transposon insertion in stcE (FIG. 3). Additionally, StcE is released into the culture supernatant by strains carrying pO157 under the same growth conditions (FIG. 3). As StcE contains a putative cleavable N-terminal signal sequence, it is possible that StcE is actively released from the bacterium by the general secretory apparatus encoded on pO157.

StcE-mediated Jurkat cell aggregation is inhibited by the addition of ion chelators such as EDTA, a broad chelator of divalent cations, and BPS, a chelator specific for zinc and iron ions (data not shown). This suggests that StcE has a requirement for one or more divalent cations, most likely zinc. This is supported by the presence of an exact match to the histidine-rich consensus active site for metalloproteases, which coordinate zinc ions for activity (see discussion).

StcE-His interacts with a human serum protein(s) of approximately 105 kDa. To identify the factor(s) in human serum responsible for mediating Jurkat cell aggregation in the presence of StcE, the 30–60% ammonium sulfate-precipitated fraction of human serum was separated on a two-dimensional gel and transferred to a PVDF membrane. Using purified StcE-His as a probe, we performed Far Western blot analysis on the PVDF membrane, detecting any interactions between StcE-His and human serum proteins with an HRP-conjugated anti-His antibody. We found that StcE-His interacts with three spots of approximately 105 kDa ranging from very acidic to very basic in isoelectric point (data not shown). Probing the same membrane with only the HRP-conjugated anti-His antibody revealed that the three spots of approximately 105 kDa were specific for StcE-His (data not shown).

To identify these proteins, the 30–60% ammonium sulfate-precipitated fraction of human serum was removed of IgG and separated on another two-dimensional gel and either special silver stained or stained by Coomassie Brilliant Blue. The most acidic of the three spots (the leftmost spot) was well isolated from other proteins and excised from the Coomassie Brilliant Blue-stained gel. This spot was digested by endoproteinase Lys-C and analyzed by MALDI-MS. A comparison of the resulting peptide pattern with known human proteins in the SWISS-PROT database revealed a match with human plasma protease C1 inhibitor.

Cleavage of C1 Inhibitor by StcE-His

Figure 4:
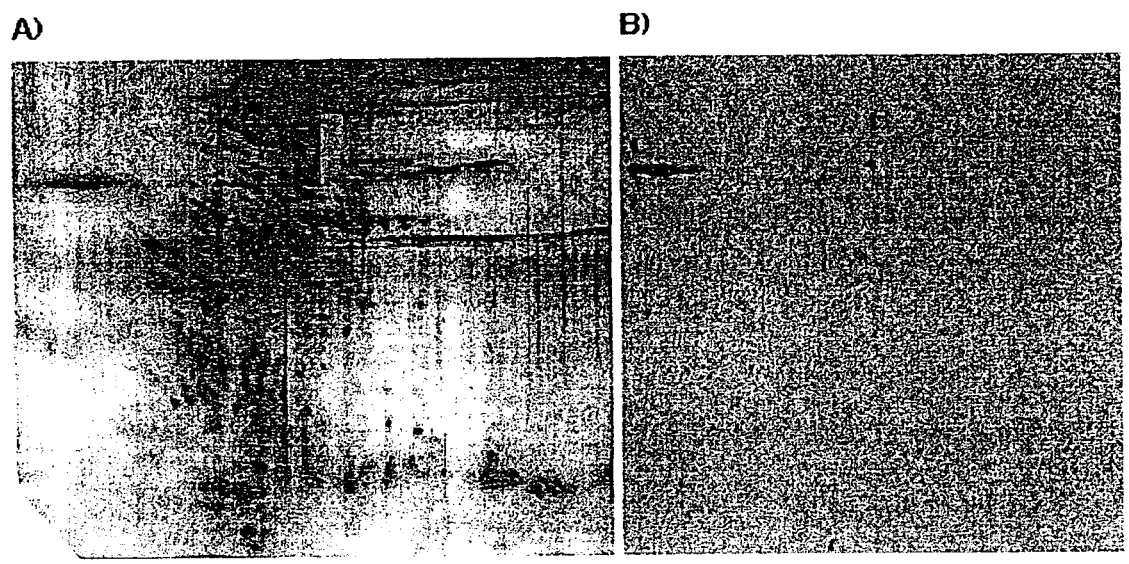
FIG. 4 shows that C1 inhibitor in human serum is cleaved by StcE.

To confirm the interaction between StcE and human C1 inhibitor and to test the possibility that StcE may proteolyze C1 inhibitor, whole and ammonium sulfate-precipitated fractions of human serum were mixed with StcE-His, separated by SDS-PAGE, and transferred to nitrocellulose for immunoblot analysis. Using an anti-human C1 inhibitor antibody, we detected the presence of C1 inhibitor in samples lacking StcE-His and the absence of C1 inhibitor in samples containing StcE-His (FIG. 4). As predicted by Jurkat cell aggregation, the 0–30% and 30–60% ammonium sulfate-precipitated fractions of human serum were enriched for C1 inhibitor compared to the 60–100% fraction. After treatment with StcE-His, however, little to no C1 inhibitor could be detected in any of the fractions. The addition of EDTA or BPS to the mixture prevented the disappearance of C1 inhibitor from the serum samples, indicating a specific requirement for divalent cations, most likely zinc, for StcE activity (data not shown).

Figure 5:
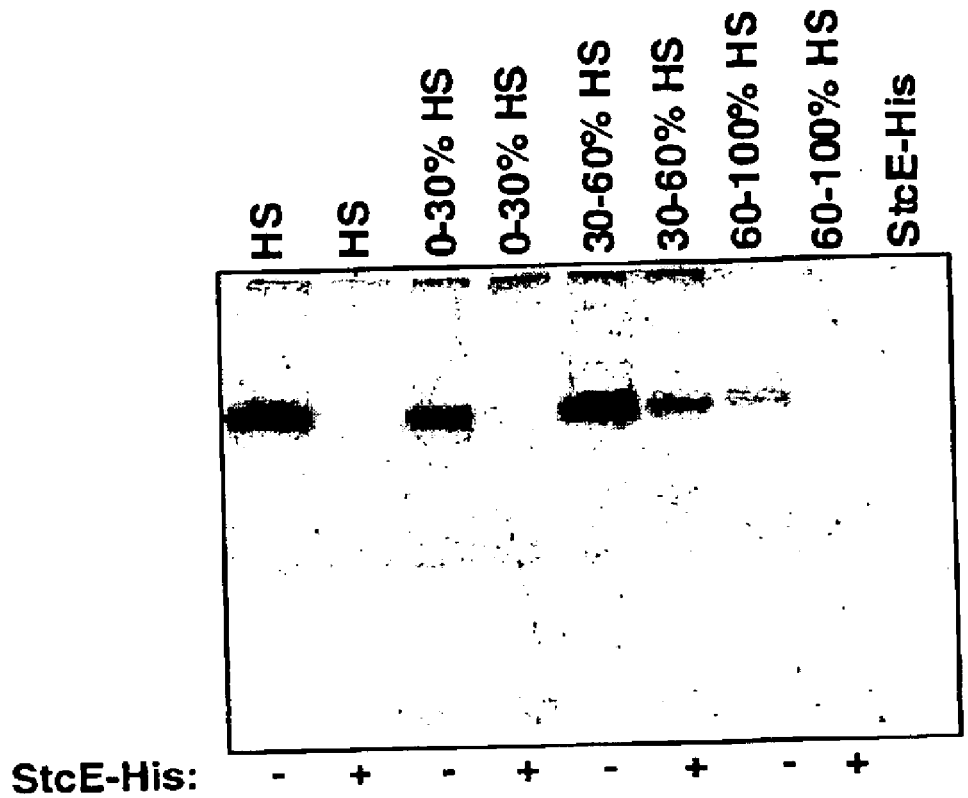
FIG. 5 shows cleavage of C1 inhibitor over time.

To confirm that the proteolysis of C1 inhibitor was a direct result of an interaction with StcE-His, we mixed purified human C1 inhibitor with StcE-His and removed aliquots of the reaction at various time points for analysis by immunoblot. Using an anti-human C1 inhibitor antibody, we detected the disappearance of a 105 kDa band corresponding to full-length C1 inhibitor and the appearance of an approximately 60 kDa cleavage product in a time-dependent manner (FIG. 5).

Examination of Patient Fecal Filtrates for StcE

Freshly passed stool samples from children with culture-positive *E. coli* O157:H7 (n=6), *Campylobacter jejuni* (n=2), Shigella B (n=2), or *Clostridium difficile* (n=2) infections were diluted 1:10 in PBS and passed through a 0.45 μm filter. Thirty μl of thawed filtrate was suspended in 1× sample buffer, heated (95–100° C. for 5 min) and electrophoresed on 8% polyacrylamide gels. Separated proteins were transferred to nitrocellulose and probed with a polyclonal antibody to StcE-His as described above. Twenty μl of the same samples was added to $1\times10^6$/ml Jurkat cells in 10% FCS and gentamicin (50 μg/ml) for 24 hours at 37° C. in 5% $CO_2$ to determine the ability of the filtrates to aggregate Jurkat cells.

Construction and Analyses of StcE E435D-His Mutant

The StcE E435D-His mutant was created using the PCR-based method of overlap extension (Horton et al. 1993). The first two PCR reactions were (i) stcE top strand primer 587 (5'-CCGCTCCGGTGAACTGGAGAATA-3') (SEQ ID NO:8) with its partner mutagenic primer 592 (5'-GACCATAATTATGACCAACATCATGACTGA-3') (SEQ ID NO:9) and (ii) stcE bottom strand primer 573 (5'-CCTTATCTGCGGAGGCTGTAGGG-3') (SEQ ID NO:10) with its partner mutagenic primer 574 (5'-TGAGTTCAGTCATGATGTTGGTCATAATTAT-3') (SEQ ID NO:11). Each reaction used 50 pM of each primer, about 100 ng of template DNA, and Deep Vent polymerase (New England Biolabs) in a 100 μl reaction. The reactions were run in a thermocycler under appropriate conditions (11) and the resulting products were purified on a 1% agarose gel using the QIA-quick Gel Extraction Kit (Qiagen). The next PCR reaction contained 5 μl each of the gel-purified fragments, along with the stcE primers 587 and 573 and Deep Vent polymerase in a 100 μl reaction. The PCR products were gel-purified as above and cut with the restriction endonucleases PmeI and BsrG1. pWL107 was also cut with PmeI and BsrG1 and the mutant PCR product was ligated into pWL107, creating pTEG1. The base substitution was confirmed by sequence analysis. pTEG1 was transformed into *E. coli* strain BL21(DE3) to create WAM2726 and StcE E435D-His was overexpressed and purified from this strain as described above. The purified protein was then analyzed for its ability to aggregate Jurkat cells as described above.

Purified C1-INH (one μg) was mixed with or without StcE-His (one μg) or StcE E435-His (one μg) overnight at room temperature in 500 μl buffer AD, precipitated with TCA (to 10%), electrophoresed on an 8% polyacrylamide gel, and transferred to nitrocellulose before analysis by immunoblot with an anti-C1-INH antibody as described above.

Purified C1-INH (500 ng) and human serum (50 μg) were electrophoresed on an 8% polyacrylamide gel in duplicate and the separated proteins were transferred to nitrocellulose for Far Western analysis. Essentially the same protocol was followed as described above with the following difference:

one blot was probed with purified StcE-His (2 μg/ml) and the other with purified StcE E435D-His (2 μg/ml).

Colony Blot Analysis

A one kb fragment of stcE was PCR amplified from pO157 using the primers stcE5'846 (5'-GAGAATAATCGAATCACTTATGCTC-3') (SEQ ID NO:12) and stcE3'1773 (5'-CGGTGGAGGAACGGCTATCGA-3') (SEQ ID NO:13) under standard reaction conditions. The PCR product was purified on a 1% agarose gel using the QIA-quick Gel Extraction Kit (Qiagen) and fluorescein-labeled using the ECL random prime labeling system (Amersham Life Science). Bacterial strains from the DEC collection, EDL933, and EDL933cu were patched onto sterile Magna Lift nylon transfer membranes (Osmonics) on LB plates and grown overnight at room temperature. Colonies were lysed by placing the membranes on 3MM Whatman paper soaked in 0.5 M NaOH. Neutralization was performed by placing the membranes first on 3MM Whatman paper soaked in 1 M Tris, pH 7.5 and then on 3MM Whatman paper soaked in 0.5 M Tris, pH 7.5/1.25 M NaCl. DNA was then crosslinked using a UV stratalinker. The blots were pre-hybridized in Church buffer (0.5 M dibasic sodium phosphate, pH 7.3, 7% SDS, 1% BSA, 1 mM EDTA) at 65° C. for one hour before the addition of the labeled probe. Hybridization proceeded overnight at 65° C. The membranes were then washed at 65° C. in 1×SSC/0.1% SDS for 15 minutes and then in 0.5× SSC/0.1% SDS for 15 minutes. The membranes were incubated with an anti-fluorescein labeled, HRP-conjugated antibody. The membrane was developed using the LumiGLO Chemiluminescent Substrate Kit (Kirkegaard and Perry Laboratories).

PCR Analysis of StcE

Oligonucleotides were designed to amplify by PCR regions of stcE to cover the length of the ~2.8 kbp promoter and gene. Primers stcE5'1 (5'-TTTACGAAACAGGTGTAAATATGTTATAAA-3') (SEQ ID NO:14) and stcE3'845 (5'-CAGTTCACCG-GAGCGGAACCA-3') (SEQ ID NO:15) covered the first third, stcE5'846 and stcE3'1773 covered the middle third, and stcE5'1774 (5'-GCTTCAGCAAGTGGAATGCAGATAC-3') (SEQ ID NO: 16) and stcE3'2798 (5'TTATTTATATACAACCCTCATTGACCTAGG-3') (SEQ ID NO: 17) covered the final third. Genomic DNA was isolated from E. coli strains DEC3A-E, DEC4A-E, DEC5A-E, EDL933, and EDL933cu using the Wizard Genomic DNA Purification Kit (Promega) as per the manufacturer's instructions. PCR was performed using 20 pM of each primer, about 100 ng of template DNA, and Deep Vent polymerase (New England Biolabs) in a 100 μl reaction. The reactions were run in a thermocycler under standard conditions. PCR products were electrophoresed on 1% agarose gels and visualized with ethidium bromide.

Isolation and Analyses of Bacterial Culture Supernatants

E. coli strains DEC3A-E, DEC4A-E, DEC5A-E, EDL933, and EDL933cu were grown in Lennox L broth at 37° C. overnight. Culture supernatants were harvested by centrifugation at 4° C. for 15 minutes at 10,000×g and filtered through a 0.45 μm filter. Supernatants were precipitated with ammonium sulfate to 75% saturation. The precipitates were centrifuged for 15 minutes at 16,000×g at 4° C. and resuspended in buffer AD. The resuspended precipitates were dialyzed against three changes of AD buffer overnight to remove residual ammonium sulfate.

Purified CI-INH (one μg) was mixed with 200 μl of ammonium sulfate-precipitated culture supernatants at room temperature overnight in a total volume of 500 μl buffer AD before precipitation with TCA (to 10%) and electrophoresis on 8% polyacrylamide gels. Separated proteins were transferred to nitrocellulose and immunoblot analysis was performed with an anti-C1-INH antibody as described above. Culture supernatants alone were separated on 8% polyacrylamide gels and transferred to nitrocellulose before immunoblot analysis was performed using an anti-StcE-His antibody as described above.

Specificity of StcE-His for C1-INH

To evaluate the specificity of StcE-His, potential target proteins (listed in Table 2), target protein (2 μg) was mixed with either StcE-His (1.28 μg) or Pseudomonas aeruginosa elastase (20 ng) (Calbiochem EC# 3.4.24.26) overnight at 37° C. in 500 μl buffer AD (20 mM Tris, pH 7.5, 100 mM NaCl, 10% glycerol, 0.01% Tween-20) and precipitated with TCA (to 10%) prior to electrophoresis on 8–10% polyacrylamide gels. Proteins in the gels were then Coomassie-stained or transferred to nitrocellulose for immunoblot analysis as above.

StcE is able to cleave both purified and serum-associated C1-INH. Only C1-INH was cleaved by StcE-His; the sizes and staining intensities of all other potential substrates were the same in the presence and absence of StcE-His. In contrast, elastase degraded most of the proteins tested. Elastase treatment of C1-INH normally produces an inactive 95 kDa product (12), whereas treatment of C1-INH with StcE-His results in ~60–65 kDa C1-INH fragment(s) (FIG. 6). This indicates that the StcE cleavage site of C1-INH is distinct from that used by elastase. We employed a sensitive fluorimetric assay based on the digestion of a BODIPY FL-labeled casein substrate (EnzChek, Molecular Probes) to analyze further the ability of StcE-His to act as a nonspecific endoprotease. Serial two-fold dilutions of StcE-His or P. aeruginosa elastase were mixed with the casein substrate per the manufacturer's instructions before fluorescent measurement of casein degradation. StcE-His was unable to degrade casein even at high protein concentrations (up to 6.4 μg/unit of volume), while elastase was able to act on casein at lower concentrations (range: 0.5 ng to 1 μg/unit of volume) (data not shown).

TABLE 2

Proteolysis of substrates incubated with StcE-His or P. aeruginosa elastase

| Substrate | StcE | Elastase |
|---|---|---|
| C1 inhibitor (Cortex Biochem, San Leandro, CA) | + | + |
| α2-antiplasmin (Calbiochem, San Diego, CA) | − | + |
| α1-antitrypsin (Sigma, St. Louis, MO) | − | + |
| α1-antichymotrypsin (Sigma, St. Louis, MO) | − | + |
| antithrombin (Enzyme Research Labs, South Bend, IN) | − | + |
| α2-macroglobulin (Calbiochem, San Diego, CA) | − | + |
| von Willebrand factor (gift from Dr. D. Mosher, UW-Madison) | − | N.D. |
| collagen IV (Rockland, Gilbertsville, PA) | − | − |
| fibronectin (Calbiochem, San Diego, CA) | − | + |
| serum albumin (New England Biolabs, Beverly, MA) | − | N.D. |
| IgA1 (Cortex Biochem, San Leandro, CA) | − | + |
| Elastin (Sigma, St. Louis, MO) | − | + |
| Gelatin (BioRad, Hercules, CA) | − | + |

N.D. = not done
Two μg of the indicated protein substrates were mixed with 1.28 μg StcE-His or 20 ng P. aeruginosa elastase overnight at 37° C. prior to electrophoresis by SDS-PAGE and staining with Coomassie Brilliant Blue. StcE was unable to digest any of the proteins tested other than Cl-INH, while P. aeruginosa elastase had activity against a broad range of targets.

Detection of StcE in Feces.

Figure 7:
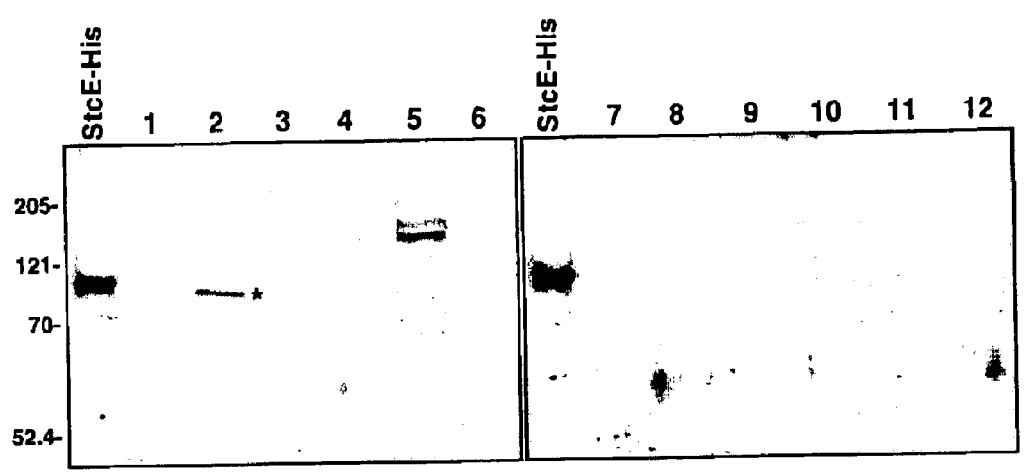
FIG. 7 is an immunoblot showing a StcE-reactive band in fecal filtrates.

The Shiga-like toxin has been identified in the feces of patients infected with E. coli O157:H7 (13, 14). To demonstrate that StcE is produced in vivo during an *E. coli* O157:H7 infection, we examined fecal filtrates collected from patients with *E. coli* O157:H7 and non-*E. coli* O157:H7-mediated diarrhea for the presence of StcE antigen and activity. Twelve fecal samples were diluted in PBS and filtered before analysis by immunoblot with polyclonal antibodies to StcE-His. A strongly reactive band with a molecular weight similar to StcE was present in the filtrate from one child infected with *E. coli* O157:H7 (FIG. 7, sample 2). Because StcE is able to mediate the aggregation of T cells, we examined the ability of the twelve fecal filtrates to aggregate Jurkat cells. Twenty µl of each filtrate was added to $5\times10^5$ Jurkat cells in the presence of 10% FCS. The one sample that contained a StcE-reactive species aggregated Jurkat cells to the same extent as 50 ng/ml purified StcE-His; all other samples were negative in this assay, even after 24 hours of incubation (data not shown).

StcE Contains a Zinc Metalloprotease Active Site.

Figures 8A, 8B:
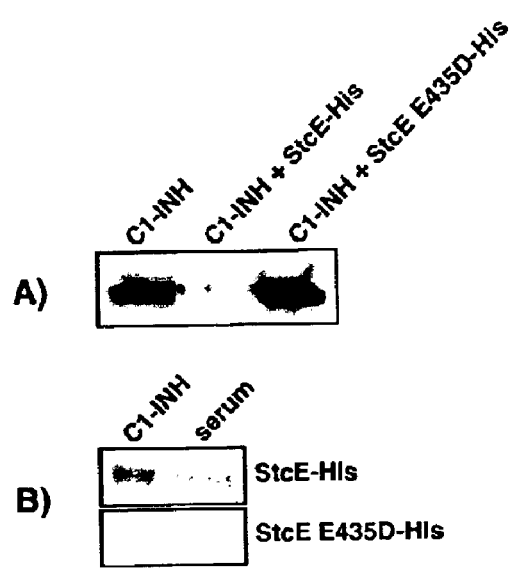
FIG. 8A shows that StcE E435D-His is unable to cleave C1-INH.
FIG. 8B shows that StcE E435D-His is unable to bind C1-INH.

As the predicted StcE amino acid sequence has a consensus $Zn^{2+}$-ligand binding site of metalloproteases (434: HEVGHNYGLGH) (SEQ ID NO:3), we examined the possibility that the glutamic acid residue at position 435 is critical for the proteolysis of C1-INH. This amino acid in other zinc metalloproteases acts as the catalytic residue for proteolysis (15) (16), and other researchers have shown that a conservative amino acid substitution from glutamic to aspartic acid disrupts the activity of the protease while maintaining its structure (15). By introducing a single change in the sequence of stcE at base 1442 from an A to a T, we created the same mutation and examined the ability of the recombinant mutant (StcE E435D-His) to digest C1-INH. While StcE-His is able to degrade C1-INH, we observed no such cleavage with the mutant protein (FIG. 8A) under the same conditions. Indeed, StcE E435D-His was unable even to bind to C1-INH or a similarly sized protein in human serum as determined by Far Western analysis (FIG. 8B), suggesting that glutamic acid 435 is necessary for both binding and cleavage of C1-INH. The StcE-mediated aggregation of Jurkat cells was also affected by the E435D mutation. Jurkat cells will aggregate in response to StcE-His at concentrations as low as 1 ng/ml, while cells treated with as much as 200 ng/ml StcE E435D-His did not aggregate (data not shown). Thus, the glutamic acid residue at position 435 is critical for StcE-mediated aggregation of Jurkat cells, as well as proteolysis of and binding to C1-INH.

Detection of StcE Among Diarrheagenic *E. coli* Strains.

In order to establish the prevalence of stcE among other pathogenic strains of *E. coli*, we examined the Diarrheagenic *E. coli* (DEC) collection, a reference set of 78 *E. coli* strains provided by Dr. Tom Whittam of the University of Pennsylvania, for the presence of stcE. This collection contains a variety of enterohemorrhagic, enteropathogenic, and enterotoxigenic *E. coli* strains of different serotypes isolated from humans, non-human primates, and other mammals that are associated with disease symptoms, including diarrhea, hemorrhagic colitis, or HUS. The DEC collection is divided into 15 subgroups based on electrophoretic type, which is indicative of the genetic similarity of one strain to another. By using colony blot analysis, we found that all O157:H7 strains of *E. coli* (DEC3 and DEC4) contain DNA that hybridizes with an internal one kb region of stcE (Table 3). Surprisingly, three of five enteropathogenic O55:H7 strains of *E. coli* (DEC5A, C, & E) also hybridized with the stcE probe. Because O157:H7 strains are thought to have evolved from an O55:H7 predecessor, this result suggests a source of the stcE gene for current O157:H7 strains of *E. coli*. None of the other strains in the DEC collection hybridized with the stcE probe by colony blot analysis.

Figure 9:
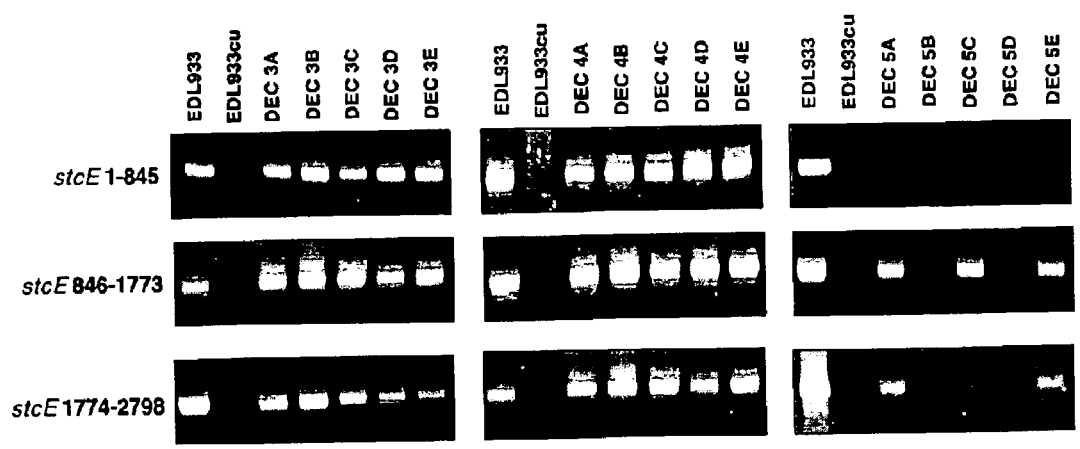
FIG. 9 shows amplification of three stcE-specific sequences from all *E. coli* isolates containing the pO157, and amplification of two of the three stcE-specific sequences.

To confirm the presence of the gene among the stcE-positive groups in the DEC collection, we isolated genomic DNA from DEC3A-E, DEC4A-E, DEC5A-E, EDL933, and EDL933cu and used oligonucleotide pairs designed to amplify regions of stcE by PCR. Three primer sets were chosen to amplify stcE and its promoter from bases 1–845, 846–1773, and 1774–2798. An appropriately-sized PCR product was amplified with all three primer pairs from EDL933, DEC3A-E, and DEC4A-E (FIG. 9). Appropriately sized products were obtained with primer pairs 846–1773 and 1774–2798 for DEC5 A, C, and E, but there were no products with primer pair 1–845 from these strains. It is possible that this region of stcE, which includes the putative promoter, is sufficiently different from stcE found on pO157 to prevent priming and amplification. DEC5B and D were negative for all three reactions.

TABLE 3

Incidence of stcE and its product in the DEC collection

| DEC Number | Predominant Serotype | Disease Category | Number of stcE positive | Number of StcE positive |
| --- | --- | --- | --- | --- |
| 1A–E | O55:H6 | EPEC | 0/5 | ND |
| 2A–E | O55:H6 | EPEC | 0/5 | ND |
| 3A | O157:H7 | EHEC | + | + |
| 3B | O157:H7 | EHEC | + | + |
| 3C | O157:H7 | EHEC | + | + |
| 3D | O157:H7 | EHEC | + | + |
| 3E | O157:H7 | EHEC | + | + |
| 4A | O157:H7 | EHEC | + | + |
| 4B | O157:H7 | EHEC | + | + |
| 4C | O157:H7 | EHEC | + | + |
| 4D | O157:H7 | EHEC | + | + |
| 4E | O157:H7 | EHEC | + | + |
| 5A | O55:H7 | EPEC | + | + |
| 5B | O55:H7 | EPEC | − | − |
| 5C | O55:H7 | EPEC | + | − |
| 5D | O55:H7 | EPEC | − | − |
| 5E | O55:H7 | EPEC | + | + |
| 6A–E | O111:H12 | EPEC | 0/5 | ND |
| 7A–E | O157:H43 | ETEC | 0/5 | 0/5 |
| 8A–E | O111:H8 | EHEC | 0/5 | ND |
| 9A–E | O26:H11 | EHEC | 0/5 | ND |
| 10A–E | O26:H11 | EHEC | 0/5 | ND |
| 11A–E | O128:H2 | EPEC | 0/5 | ND |
| 12A–E | O111:H2 | EPEC | 0/5 | ND |
| 13A–E | O128:H7 | ETEC | 0/5 | ND |
| 14A–E | O128:H21 | EPEC | 0/5 | ND |
| 15A–E | O111:H21 | EPEC | 0/5 | ND |

Using a one kb probe internal to stcE, colony blot analyses were performed to determine which strains in the DEC collection contained stcE. Strains that were positive for the gene were checked for secretion of StcE as well proteolytic activity against C1-INH. Strains in bold contained the gene and produced the protein. Strains in italics contained the gene but lacked detectable protein. All other strains in the DEC collection were negative for stcE.
ND = not done.

Figure 10:
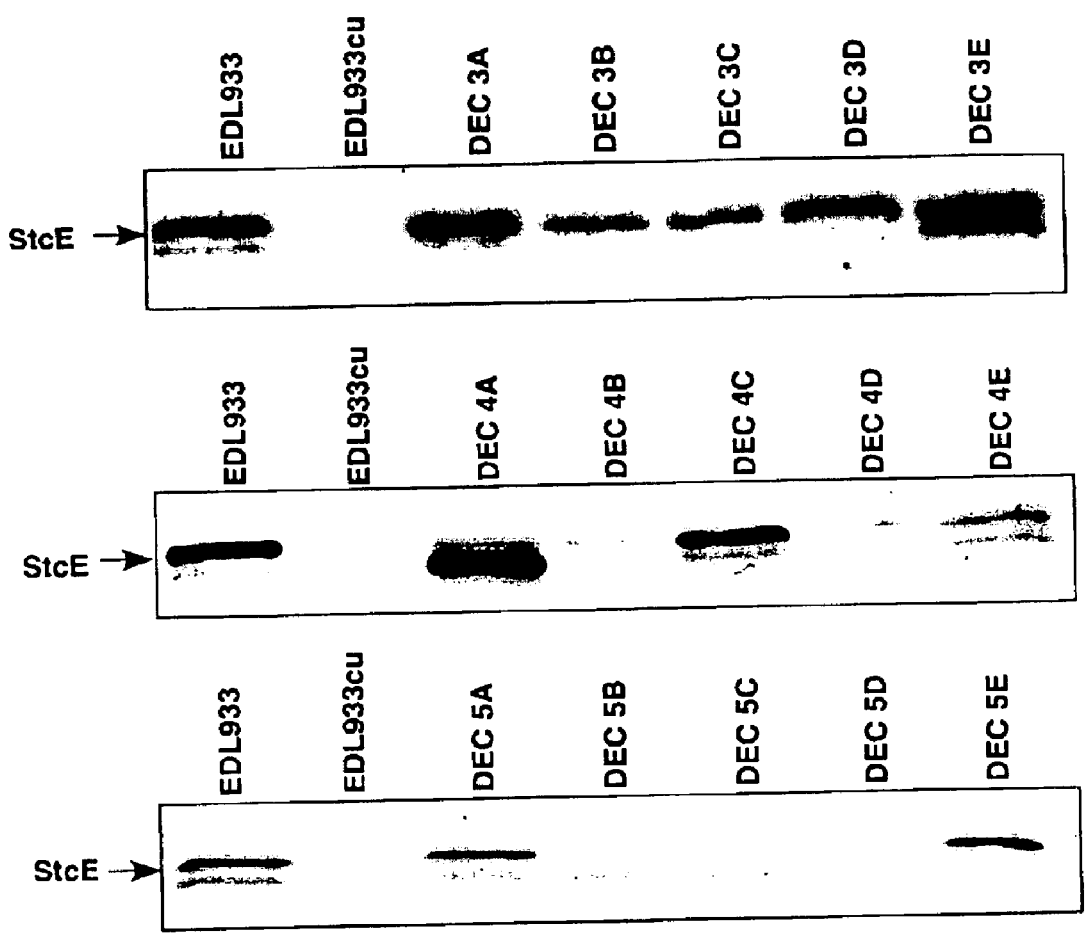
FIG. 10 shows an immunoblot of culture supernatants probed with a polyclonal antibody to StcE.
Figure 11:
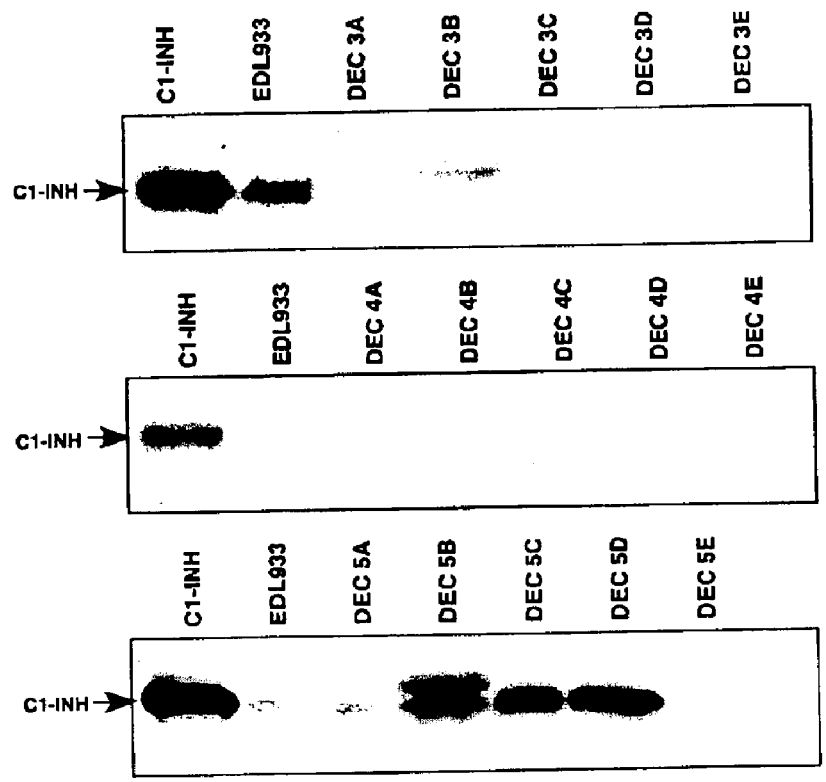
FIG. 11 shows an immunoblot of C1-INH following incubation with culture supernatants, probed with anti-C1-INH antibody.

Because previous experiments showed that StcE is released into the culture medium by EDL933 (FIG. 3), we examined whether the stcE-positive strains from the DEC collection also release StcE into the culture medium. We grew DEC3A-E, DEC4A-E, DEC5A-E, EDL933, and EDL933cu overnight in Lennox L broth at 37° C., harvested and concentrated the culture supernatants 100-fold. By immunoblot analysis we were able to detect StcE-reactive antigen in the supernatants of all stcE-positive strains and DEC5C (FIG. 10). The intensity of the reactive band varied from strain to strain and seemed to be stronger in the DEC3 group. To test if the bacterial-conditioned culture supernatants contained C1-INH proteolytic activity, we mixed purified C1-INH with the supernatants overnight and examined substrate cleavage by immunoblot. Again, all stcE-positive strains except DEC5C were able to degrade C1-INH (FIG. 11). Interestingly, DEC5B converted C1-INH from a single band to a doublet; this is unlikely to be related to StcE activity and the significance of this is unknown. It appears that DEC5C is unable to release StcE into the culture medium, although it contain stcE-like DNA. This may be due to a lack of expression of the gene or release of the protein from the cell.

1. Perna, N. T., Plunkett III, G., Burland, V., Mau, B., Glasner, J. D., Rose, D. J., Kirkpatrick, H. A., Postal, G., Hackett, J., Klink, S., Boutin, A., Shao, Y., Miller, L., Grotbeck, E. J., Davis, N. W., Lim, A., Dimalanta, E. T., Potamousis, K. D., Apodaca, J., Anantharaman, T. S., Lin, J., Yen, G., Schwartz, D. C., Welch, R. A. & Blattner, F. R. (2001) *Nature* 409, 529–533.
2. Waytes, A. T., Rosen, F. S. & Frank, M. M. (1996) *N. Engl. J. Med.* 334, 1630–1634.
3. Caliezi, C., Wuillemin, W. A., Zeerleder, S., Redondo, M., Eisele, B. & Hack, C. E. (2000) *Pharmacol. Rev.* 52, 91–112.
4. Poulle, M., Burnouf-Radosevich, M. & Burnouf, T. (1994) *Blood Coagulation & Fibrinolysis* 5, 543–9.
5. Kuno, K., Terashima, Y. & Matsushima, K. (1999) *Journal of Biological Chemistry* 274, 18821–6.
6. Gadek, J. E., Hosea, S. W., Gelfand, J. A., Santaella, M., Wickerhauser, M., Triantaphyllopoulos, D. C. & Frank, M. M. (1980) *N. Engl. J. Med.* 302, 542–546.
7. Lorenzo, V. D. & Timmis, K. N. (1994) in *Bacterial Pathogenesis*, eds. Clark, V. L. & Bavoil, P. M. (Academic Press, San Diego), Vol. 235, pp. 386–405.
8. O'Farrell, P. H. (1975) *J Biol Chem* 250, 4007–21.
9. Bauer, M. E. & Welch, R. A. (1996) *Infect. Immun.* 64, 167–175.
10. Burland, V., Shao, Y., Perna, N. T., Plunkett, G., Sofia, H. J. & Blattner, F. R. (1998) *Nucleic Acids Research* 26, 4196–4204.
11. Roesch, P. L. & Blomfield, I. C. (1998) *Molecular Microbiology* 27, 751–61.
12. Catanese, J. & Kress, L. F. (1984) *Biochim. Biophys. Acta* 789, 37–43.
13. Karmali, M. A., Petric, M., Steele, B. T. & Lim, C. (1983) *Lancet* 1, 619–620.
14. Caprioli, A., Luzzi, I., Gianviti, A., Russmann, H. & Karch, H. (1995) *J. Med. Microbiol.* 43, 348–353.
15. Jiang, W. & Bond, J. S. (1992) *FEBS Lett* 312, 110–114.
16. Jung, C.-M., Matsushita, O., Katayama, S., Minami, J., Sakurai, J. & Okabe, A. (1999) *J. Bact.* 181, 2816–2822.

What is claimed is:

1. An isolated polypeptide comprising the amino acid sequence of amino acid sequence of amino acid residues 230–630 of SEQ ID NO:2, wherein the polypeptide comprises a StcE specific immunogen or has the ability to bind to and cleave C1 esterase inhibitor.

2. The polypeptide of claim 1, wherein the polypeptide comprises amino acid residues 85–734 of SEQ ID NO:2.

3. The polypeptide of claim 1, wherein the polypeptide comprises amino acid residues 24–886 of SEQ ID NO:2.

4. The polypeptide of claim 1, wherein the polypeptide has the ability to bind to and cleave C1 esterase inhibitor.

5. An isolated polypeptide comprising an amino acid sequence having at least 95% amino acid identity to amino acid residues 24–886 of SEQ ID NO:2, the polypeptide comprising a sequence corresponding with and identical to amino acids 434–444 of SEQ ID NO:2, the polypeptide having the ability to bind to and cleave C1 esterase inhibitor.

6. An isolated polypeptide, the amino acid sequence of which consists of at least 17 consecutive amino acid residues of SEQ ID NO:2, wherein the polypeptide consists of a StcE specific immunogen.

7. The polypeptide of claim 6, wherein the amino acid sequence consists of at least 25 consecutive amino acid residues of SEQ ID NO:2.

8. The polypeptide of claim 6, wherein the amino acid sequence consists of at least 40 consecutive amino acid residues of SEQ ID NO:2.

9. The polypeptide of claim 6, wherein the amino acid sequence comprises amino acid residues 430–446 of SEQ ID NO:2.

10. The polypeptide of claim 6, wherein the amino acid sequence comprises amino acid residues 421–446 of SEQ ID NO:2.

11. The polypeptide of claim 6, wherein the amino acid sequence comprises amino acid residues 408–448 of SEQ ID NO:2.

* * * * *